United States Patent
Londono et al.

(10) Patent No.: US 12,308,111 B2
(45) Date of Patent: May 20, 2025

(54) METHODS FOR INTERACTIVE ANNOTATION OF MEDICAL IMAGES IN A CLIENT-SERVER ARCHITECTURE

(71) Applicant: GE Precision Healthcare LLC, Wauwatosa, WI (US)

(72) Inventors: Jorge Hernandez Londono, Versailles (FR); Vincent Morard, Chassieu (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 372 days.

(21) Appl. No.: 17/835,430

(22) Filed: Jun. 8, 2022

(65) Prior Publication Data

US 2023/0402156 A1 Dec. 14, 2023

(51) Int. Cl.
| | | |
|---|---|---|
| G16H 30/40 | (2018.01) | |
| G06T 7/00 | (2017.01) | |
| G06T 7/11 | (2017.01) | |
| G06V 10/25 | (2022.01) | |
| G06V 10/82 | (2022.01) | |

(52) U.S. Cl.
CPC ........... *G16H 30/40* (2018.01); *G06T 7/0012* (2013.01); *G06T 7/11* (2017.01); *G06V 10/25* (2022.01); *G06V 10/82* (2022.01); *G06T 2200/24* (2013.01); *G06T 2207/20081* (2013.01); *G06T 2207/20084* (2013.01)

(58) Field of Classification Search
CPC .......... G16H 30/40; G16H 40/67; G06T 7/11; G06T 2207/20084; G06T 2207/20104; G06T 7/0012; G06V 10/82

See application file for complete search history.

(56) References Cited

U.S. PATENT DOCUMENTS

| | | | | |
|---|---|---|---|---|
| 9,928,875 | B2 * | 3/2018 | Choi | G06V 20/46 |
| 10,147,185 | B2 * | 12/2018 | Riklin Raviv | G16H 50/50 |
| 10,825,172 | B2 * | 11/2020 | Pauly | A61B 5/7267 |

(Continued)

OTHER PUBLICATIONS

Peng S. et al., Weakly Supervised Segmentation of Vertebral Bodies with Iterative Slice-Propagation, Oct. 13, 2019, Springer, Lecture Notes in Computer Science() vol. 11795 https://doi.org/10.1007/978-3-030-33391-1_14 (Year: 2019).*

(Continued)

*Primary Examiner* — Molly Wilburn
*Assistant Examiner* — Jordan McKenzie Elliott
(74) *Attorney, Agent, or Firm* — Fletcher Yoder, P.C.

(57) ABSTRACT

Presently disclosed are systems and methods for extrapolating a predictive two-dimensional (2D) segmentation to indicate a predicted region of interest (ROI) in a 2D medical image frame rendered from a set of three-dimensional (3D) medical scan data, wherein the predictive segmentation is based on a user-defined 2D segmentation that annotates the ROI in another image frame rendered from the 3D medical scan data. Present embodiments can utilize a user-defined or user-modified 2D segmentation of a frame to extrapolate predicted 2D segmentations for all of the other frames within a set of 3D medical scan data. This enables present embodiments to effectively annotate the ROI in a series of 2D medical image frames with minimal input from a clinician, reducing the amount of time the clinician spends analyzing the 3D medical scan data.

19 Claims, 16 Drawing Sheets

(56) References Cited

U.S. PATENT DOCUMENTS

| | | | |
|---|---|---|---|
| 11,049,289 B2* | 6/2021 | Morard | G06T 7/12 |
| 11,875,898 B2* | 1/2024 | Shi | G16H 30/40 |
| 12,016,696 B2* | 6/2024 | Labiche | A61B 5/1032 |
| 12,211,204 B2* | 1/2025 | Xu | G06T 7/30 |
| 2009/0136096 A1* | 5/2009 | Sirohey | G06T 19/00 |
| | | | 382/128 |
| 2020/0082930 A1* | 3/2020 | De Francesco | G16H 10/60 |
| 2020/0160979 A1* | 5/2020 | Lyman | G06F 18/217 |
| 2020/0167930 A1* | 5/2020 | Wang | G06N 3/08 |
| 2020/0226422 A1* | 7/2020 | Li | G06N 3/04 |
| 2020/0226798 A1* | 7/2020 | Morard | G06T 11/60 |
| 2020/0250826 A1* | 8/2020 | Cohen Maimon | G16H 30/20 |
| 2020/0320659 A1* | 10/2020 | Whiting | B25J 19/023 |
| 2020/0320778 A1* | 10/2020 | Duan | G06T 15/30 |
| 2020/0410721 A1* | 12/2020 | Farri | G06F 40/279 |
| 2021/0012883 A1* | 1/2021 | Bidulock | G16H 10/40 |
| 2021/0192279 A1* | 6/2021 | Laaksonen | G16H 30/20 |
| 2021/0304402 A1* | 9/2021 | Morgas | G06T 7/12 |
| 2022/0223445 A1* | 7/2022 | Avishai | H01L 21/67288 |
| 2022/0284609 A1* | 9/2022 | Shree | G06T 7/33 |
| 2022/0318991 A1* | 10/2022 | Sperandio | G16H 30/40 |
| 2023/0087363 A1* | 3/2023 | Pardasani | G16H 50/30 |
| | | | 382/128 |
| 2023/0110806 A1* | 4/2023 | Bala | G06N 3/0464 |
| | | | 382/131 |
| 2023/0237647 A1* | 7/2023 | Xu | G06T 7/0012 |
| | | | 382/128 |
| 2023/0245753 A1* | 8/2023 | Kumar | G06V 10/7715 |
| | | | 705/2 |
| 2024/0054639 A1* | 2/2024 | Nadeem | G06T 7/0012 |
| 2024/0127410 A1* | 4/2024 | Lin | G06T 7/11 |
| 2024/0203567 A1* | 6/2024 | Ruiz | G06T 3/40 |
| 2024/0298995 A1* | 9/2024 | Flexman | A61B 6/467 |

OTHER PUBLICATIONS

Mario Amrehn et al. / UI-Net: Interactive Artificial Neural Networks, Eurographics Workshop on Visual Computing for Biology and Medicine (2017) (Year: 2017).*

Peng, S. et al. (2019). Weakly Supervised Segmentation of Vertebral Bodies with Iterative Slice-Propagation. In: Wang, Q., et al. Domain Adaptation and Representation Transfer and Medical Image Learning with Less Labels and Imperfect Data. Dart MIL3ID 2019 2019. Lecture Notes in Computer Science() (Year: 2019).*

Peng, S. et al. (2019). Weakly Supervised Segmentation of Vertebral Bodies with Iterative Slice—Propagation. In: Wang, Q., et al. Domain Adaptation and Representation Transfer and Medical Image Learning with Less Labels and Imperfect Data. https://doi.org/10.1007/978-3-030-33391-1_14 (Year: 2019).*

U.S. Appl. No. 17/654,221, filed Dec. 20, 2021, Nicolas Gogin.

U.S. Appl. No. 17/649,829, filed Feb. 3, 2022, Vincent Morard.

* cited by examiner

METHODS FOR INTERACTIVE ANNOTATION OF MEDICAL IMAGES IN A CLIENT-SERVER ARCHITECTURE

BACKGROUND

The subject matter disclosed herein relates to the annotation of medical images, and more specifically, to the annotation of medical images in a cloud-based architecture.

Clinical decisions are often derived from an analysis of medical imaging data. In the radiology domain, this typically involves the annotation of medical image data to indicate at least one region of interest (ROI). Medical image analysis is typically performed at the request of a referring physician for a specific purpose, such as the detection, assessment, and progression of anatomical abnormalities (e.g., lesions, aneurysms, atrophies). To perform such analyses, the ROI must first be accurately and robustly separated from other less relevant data, which is typically performed by a clinician using a manual annotation tool that is integrated into medical imaging software. Additionally, such medical imaging software is often locally installed on a desktop or laptop computing device of a hospital or other medical facility, which can result in delays in image analysis when the local computing system is unavailable.

BRIEF DESCRIPTION

Certain examples commensurate in scope with the originally claimed subject matter are summarized below. These examples are not intended to limit the scope of the claimed subject matter, but rather these examples are intended only to provide a brief summary of possible examples. Indeed, the subject matter may encompass a variety of forms that may be similar to or different from the examples set forth below.

In an embodiment, a computing system for performing real-time predictive two-dimensional (2D) segmentation of 2D medical image frames includes at least one networking device; at least one memory configured to store an application that includes a user interface and a set of trained annotation extrapolation neural networks (AENNs); and at least one processor configured to execute stored instructions to perform actions. These actions include receiving, via the at least one networking device, a first two-dimensional (2D) medical image frame, and a second 2D medical image frame adjacent to the first 2D medical image frame within a set of three-dimensional (3D) medical scan data; and presenting, via the user interface, the first 2D medical image frame. The actions include receiving, via the user interface, a first user interaction annotating a region of interest (ROI) in the first 2D medical image frame; and presenting, via the user interface, the first 2D medical image frame with a first user-defined 2D segmentation overlaid to annotate the ROI in the first 2D medical image frame based on the first user interaction. The actions include providing, as input to the set of trained AENNs, the first 2D medical image frame, the second 2D medical image frame, and the first user-defined 2D segmentation; and receiving, as output from the set of trained AENNs, a first predicted 2D segmentation indicating a predicted ROI in the second 2D medical image frame. The actions further include presenting, via the user interface, the second 2D medical image frame with the first predicted 2D segmentation overlaid to indicate the predicted ROI in the second 2D medical image frame.

In an embodiment, a method for predictive two-dimensional (2D) segmentation of medical image frames includes determining a first two-dimensional (2D) medical image frame from a set of three-dimensional (3D) medical scan data; determining a first user-defined 2D segmentation that annotates a region of interest (ROI) in the first 2D medical image frame based on a first user interaction; and determining a second 2D medical image frame adjacent to the first 2D medical image frame in the set of 3D medical scan data. The method includes providing, as input to a set of trained annotation extrapolation neural networks (AENNs), the first 2D medical image frame, the second 2D medical image frame, and the first user-defined 2D segmentation; and receiving, as output from the trained AENNs, a first predicted 2D segmentation indicating a predicted ROI in the second 2D medical image frame.

In an embodiment, a computing system includes at least one memory configured to store a set of trained annotation extrapolation neural networks (AENNs), and at least one processor configured to execute stored instructions to perform actions. The actions include providing, as input to the set of trained AENNs, a first two-dimensional (2D) medical image frame rendered from a first slice of three-dimensional (3D) medical scan data, a second 2D medical image frame rendered from a second slice adjacent to the first slice in the 3D medical scan data, and a first user-defined 2D segmentation annotating a region of interest (ROI) in the first 2D medical image frame; and receiving, as output from the set of trained AENNs, a first predicted 2D segmentation indicating a predicted ROI in the second 2D medical image frame. The actions include providing, as input to the set of trained AENNs, the second 2D medical image frame, a third 2D medical image frame rendered from a third slice adjacent to the second slice in the 3D medical scan data, and the first predicted 2D segmentation; and receiving, as output from the set of trained AENNs, a second predicted 2D segmentation indicating a predicted ROI in the third 2D medical image frame.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
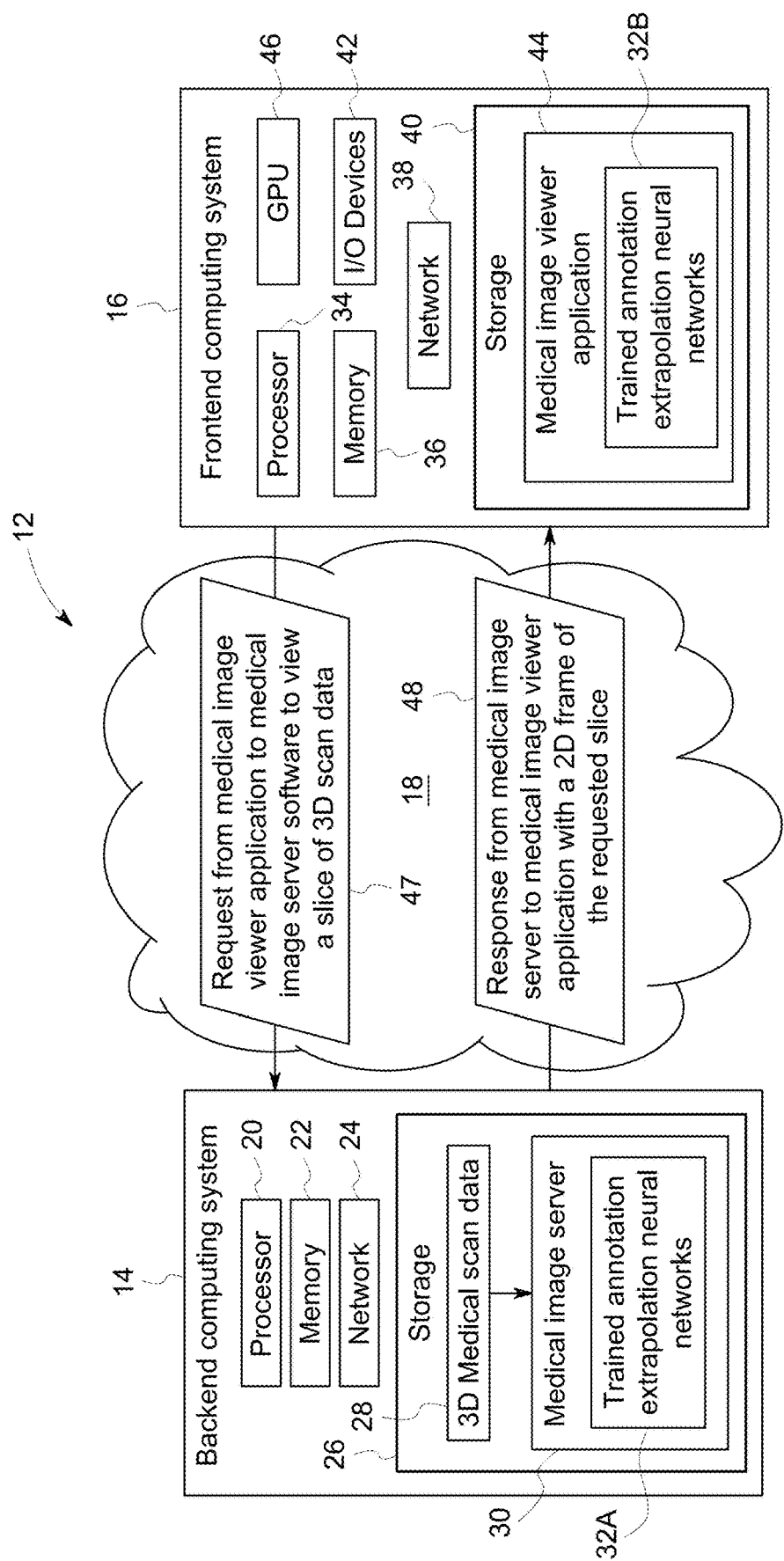
FIG. 1 is a diagram of a client-server architecture for medical image processing and analysis, in accordance with embodiments of the present technique.

One or more specific examples will be described below. In an effort to provide a concise description of these examples, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various aspects of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed examples.

Present embodiments are generally directed to system and methods for real-time interactive annotation in a client-server architecture, such as a cloud-based, client-server architecture. In the client-server architecture, at least one backend server is deployed to host medical imaging server software, and a clinician can access services provided by the backend server using a suitable application hosted by a frontend computing device (e.g., a desktop or laptop computer) of the clinician that is communicatively coupled to the backend server. The backend server stores three-dimensional (3D) medical scan data, while the clinician interacts with the application of their respective frontend computing device to request two-dimensional (2D) slices of the 3D medical scan data from the backend server. Based on the requests received from the frontend computing device, the backend server renders corresponding 2D images from the 3D medical scan data and returns the rendered images to the application of the frontend computing device to be presented to the clinician for analysis. It is recognized that this client-server architecture provides greater flexibility to scale with the number of users. However, it is also presently recognized that, since most or all of the processing is typically confined to the backend server, this architecture also imposes constraints, especially with respect to real-time annotation tools.

While certain context-specific algorithms can be used segment ROIs, such as anatomical features or pathological structures (e.g., lesion, tumors, cysts, and nodules), it is presently recognized that the predicted segmentations generated by these algorithms are imperfect due to the variability in virtually all sources of medical data. Moreover, factors, such as scale, noise, motion, partial voluming, and other artifacts, hamper the accuracy and precision of these segmentation algorithms. In many practical applications, the main issue with segmentations obtained from these segmentation algorithms is not whether they are accurate based on a numerical criterion, but rather, whether the segmentation is correct in the opinion of the clinician. Accordingly, it is recognized that, there is a need to provide a flexible and intuitive tool that enables clinicians to easily, efficiently, and correctly segment ROIs in medical images.

More specifically, present embodiments are directed to a client-server architecture and methods for extrapolating a predictive 2D segmentation that indicates a predicted ROI in a 2D medical image frame rendered from a 3D medical scan, wherein the predictive 2D segmentation is determined based on a user-defined segmentation that annotates the ROI in another image frame rendered from the 3D medical scan. Certain embodiments enable real-time predictive 2D segmentation, while other embodiments enable backend predictive 2D segmentation. As used herein, "real-time predictive 2D segmentation" refers to a predicted segmentation locally generated by a frontend computing device of the client-server architecture to indicate a predicted ROI in a 2D medical image frame. By comparison, "backend predictive 2D segmentation" refers to a predicted segmentation generated by a backend computing system of the client-server architecture to indicate a predicted ROI in a 2D medical image frame. As used herein, a "predictive segmentation" or "predicted annotation" refers to an indication of the location(s) of a ROI in a 2D medical image that is predicted by the disclosed system, and once the predictive segmentation or predictive annotation has been validated by a clinician, it may be referred to herein as an "actual annotation" or simply an "annotation". As used herein, the term "frame" refers to a 2D image that is rendered from a particular slice of 3D medical scan data. As such, it may be appreciated that the 2D image frames discussed herein are distinct from 2D medical images captured using a standard 2D medical imaging technique, such as a traditional 2D X-ray image.

Those skilled in the art will appreciate that annotation tools for medical images typically operate via interpolation, in which a segmentation may be predicted for a given medical image frame based on the combination of at least a first user-defined segmentation of an image that precedes the given frame in the 3D medical scan data and a second user-defined segmentation of a frame that follows the given frame in the 3D medical scan data. In contrast, present embodiments operate via extrapolation, in which a single user-defined 2D segmentation of a medical image frame is extrapolated using deep learning techniques to generate predicted 2D segmentations for one or more other image frames within a set of 3D medical scan data. This enables present embodiments to effectively annotate the ROI in a series of 2D medical image frames with minimal input from a clinician to provide the initial user-defined 2D segmentation, reducing the amount of time the clinician spends analyzing the 3D medical scan data, as well as reducing the number of inputs that the clinician needs to provide to annotate the ROI in the 3D medical scan data.

With the foregoing in mind, FIG. 1 illustrates an embodiment of client-server architecture 12 for medical image processing and analysis. The client-server architecture 12 generally includes at least one backend computing system 14 and at least one frontend computing system 16 that are communicatively coupled via a suitable network 18 (e.g., a local area network (LAN), a wide area network (WAN), virtual private networks (VPN), the internet). In some embodiments, the backend computing system 14 may include at least one server deployed on a LAN of a medical facility. For embodiments in which the client-server architecture 12 is particularly a cloud-based client-server architecture, the backend computing system 14 may include a rack-mounted servers deployed at a remote data center. The frontend computing system 16 may include a desktop or laptop computer of a clinician, for example, deployed on the LAN of a medical facility or coupled to the backend computing system 14 via a suitable network connection.

The backend computing system 14 generally includes at least one processor 20, at least one memory 22 (e.g., random access memory (RAM), read-only memory (ROM)), at least one networking device 24 (e.g., a wireless networking card, an Ethernet networking card), and at least one storage 26 (e.g., a hard disk device, a solid state disk device, a flash memory device). The processor 20 may include one or more central processing units (CPUs), each having one or more processing cores configured to execute instructions and process data loaded into the memory 22 from the storage 26. The storage 26 is configured to store 3D medical scan data 28, such as medical scan data from a computerized tomography (CT) scan performed by the medical facility. The storage 26 also stores instructions of a medical image server 30 that generally renders 2D medical image frames from the 3D medical scan data 28, which are then served to the frontend computing system 16 to be viewed and analyzed by the clinician. Additionally, in certain embodiments, the storage 26 also stores trained annotation extrapolation neural networks (AENNs) 32A of the medical image server 30, which are discussed in greater detail below.

The frontend computing system 16 generally includes at least one processor 34, at least one memory 36 (e.g., random access memory (RAM), read-only memory (ROM)), at least one networking device 38 (e.g., a wireless networking card, an Ethernet networking card), and at least one storage 40 (e.g., a hard disk device, a solid state disk device, a flash memory device). Additionally, the frontend computing system 16 includes input/output (I/O) devices 42, such as a keyboard, mouse, touchpad, touchscreen, speakers, displays, and so forth, which enable the clinician to provide inputs to, and receive the outputs of, the frontend computing system 16. In certain embodiments, the frontend computing system 16 includes at least one graphics processing unit 46 (GPU) that is generally configured to perform graphical processing to present images on display devices of these frontend computing system 16. As discussed below, in certain embodiments, the GPU 46 of the frontend computing system 16 can be used to perform computations during a real-time predictive 2D segmentation of a 2D medical image frame. The storage 40 stores instructions of a medical image viewer application 44, which generally presents the 2D medical image frames received from the backend computing system 14 to be viewed and analyzed by the clinician. In some embodiments, the medical image viewer application 44 may specifically be executed within an internet browser application of the frontend computing system 16, such as via a suitable plug-in. Additionally, in certain embodiments, the storage 40 also stores trained annotation extrapolation neural networks (AENNs) 32B of the medical image viewer application 44, which are discussed in greater detail below.

The medical image server 30 of the backend computing system 14 is generally designed to receive, via the network 18, requests 47 from the medical image viewer application 44 to view a particular 2D slice of 3D medical scan data 28 stored in the storage 26. In reply, the medical image server 30 of the backend computing system 14 is generally designed to provide responses 48, via the network 18, to the medical image viewer application 44 that include a rendered 2D medical image frame (hereinafter "2D frame") determined by the processor 20 of the backend computing system 14 based on the stored 3D medical scan data 28 (hereinafter "3D scan data") and the received request.

Figure 2:
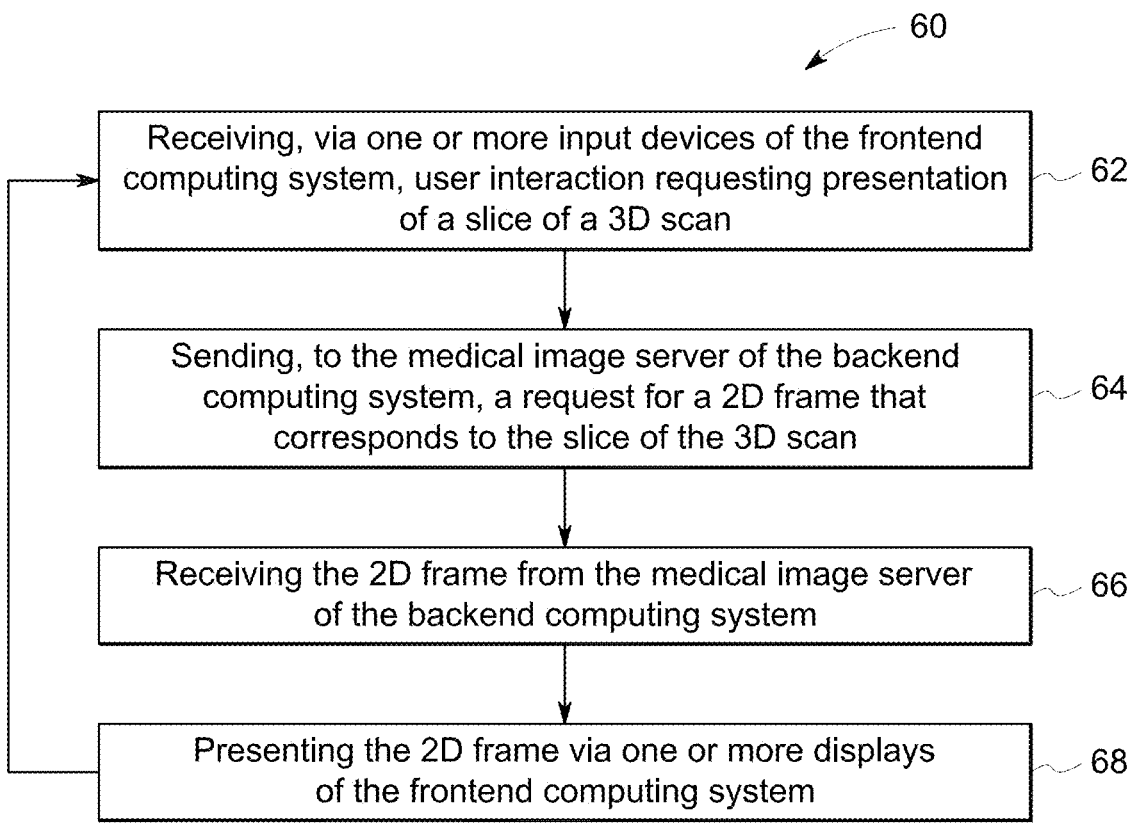
FIG. 2 is a flow diagram of a process whereby an application of a frontend computing system of the client-server architecture requests and receives 2D medical image frames from the backend computing system of the client-server architecture, wherein the 2D medical image frames are rendered by the backend computing system from 3D medical scan data, in accordance with embodiments of the present technique.

FIG. 2 illustrates an embodiment of a process 60 whereby the medical image viewer application 44 of the frontend computing system 16 of the client-server architecture 12 requests and receives 2D frames of a 3D scan from the backend computing system 14. The process 60 of FIG. 2 is discussed with reference to elements illustrated in FIG. 1. For the illustrated embodiment, the process 60 begins with the medical image viewer application 44 receiving (block 62), via at least one of the I/O devices 42 of the frontend computing system 16, user interaction requesting presentation of a slice of a 3D scan. The medical image viewer application 44 subsequently sends (block 64), to the medical image server 30 of the backend computing system 14, a request for a 2D frame that corresponds to the slice of the 3D scan. The medical image viewer application 44 receives (block 66) the 2D frame from the medical image server 30 of the backend computing system 14, and then presents (block 68) the received 2D frame via one or more displays of the frontend computing system 16.

Figure 3:
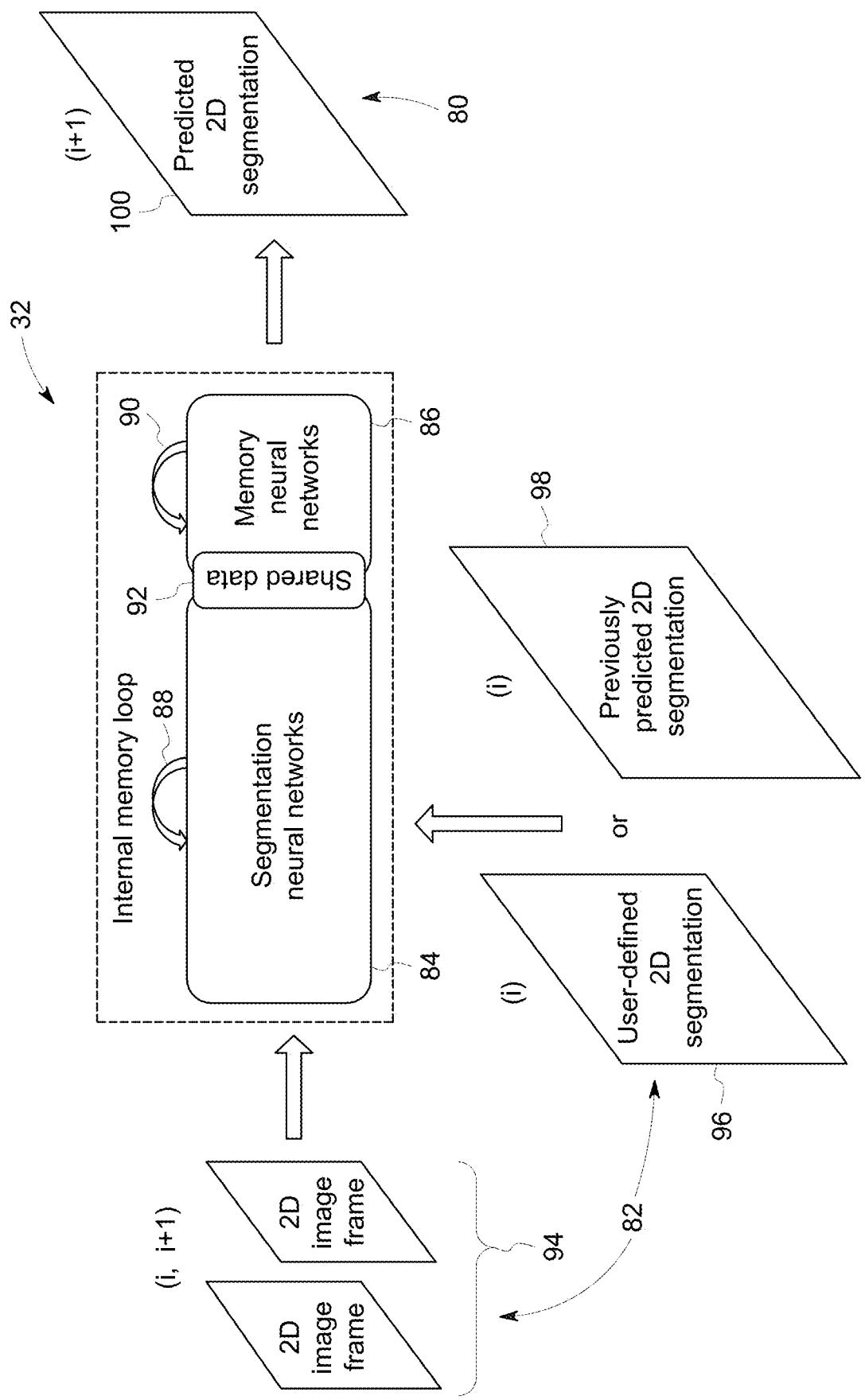
FIG. 3 is a diagram of annotation extrapolation neural networks (AENNs) that have been trained to determine a predicted 2D segmentation for a 2D medical image frame based on a set of inputs, in accordance with embodiments of the present technique.

FIG. 3 is a diagram representing annotation extrapolation neural networks (AENNs) 32 that have been trained to determine a predicted 2D segmentation for a 2D medical image frame as an output 80 based on a set of inputs 82. As noted herein, for embodiments that provide real-time predictive 2D segmentation at the frontend computing system 16, the trained AENNs 32B may be stored in the storage 40 and/or memory 36 of the frontend computing system 16, while for embodiments that provide backend predictive 2D segmentation, the trained AENNs 32A may be stored in the storage 26 and/or memory 22 of the backend computing system 14.

For the embodiment illustrated in FIG. 3, the trained AENNs 32 include two deep learning neural networks: a set of segmentation neural networks 84, and a set of memory neural networks 86. In some embodiments, the segmentation neural networks 84 are generally trained to generate predictive 2D segmentations by projecting a ROI indicated in a user-defined 2D segmentation of a first frame, or indicated in a previously predicted 2D segmentation of a first frame, to an adjacent frame based on similarities in patterns between the two adjacent frames. The memory neural networks 86 are trained to regularize the predictive 2D segmentations based on previously generated 2D segmentations. For the illustrated embodiment, the segmentation neural networks 84 and the memory neural networks 86 include respective internal memory loops, as indicated by the arrows 88 and and the segmentation neural networks 84 and the memory neural networks 86 share data (e.g., outputs/inputs, internal states) during operation, as indicated by the block 92.

For the illustrated embodiment, the inputs 82 to the AENNs 32 include any two adjacent frames 94 rendered by the backend computing system 14 from 3D scan data 28. The inputs 82 further include either a user-defined 2D segmentation 96 indicating a ROI in one of the adjacent frames 94 based on user interactions received from a clinician via a user interface of the medical image viewer application 44 of the frontend computing system 16, or a previously predicted 2D segmentation 98 generated by the AENNs 32 to indicate a ROI in one of the adjacent frames 94. In certain embodiments, in place of a user-defined 2D segmentation, one or more user interactions received to define the user-defined 2D segmentation (e.g., mouse clicks and drags over various locations of the presented image frame, tools selections, various annotations added by the clinician) may instead be provided as part of the inputs 82 to the AENNs 32. Based on the weights entrained into the AENNs 32 during training, as discussed below, the AENNs 32 process the inputs 82 to generate a predictive 2D segmentation 100 that indicates the ROI in the second frame of the adjacent frames 94. In certain embodiments directed to real-time predictive 2D segmentation at the frontend computing system 16, the GPU 46 of the frontend computing system 16 may be used to enhance processing efficiency and/or reduce run-time for calculations related to the AENNs 32 during operation and/or training.

Figure 4:
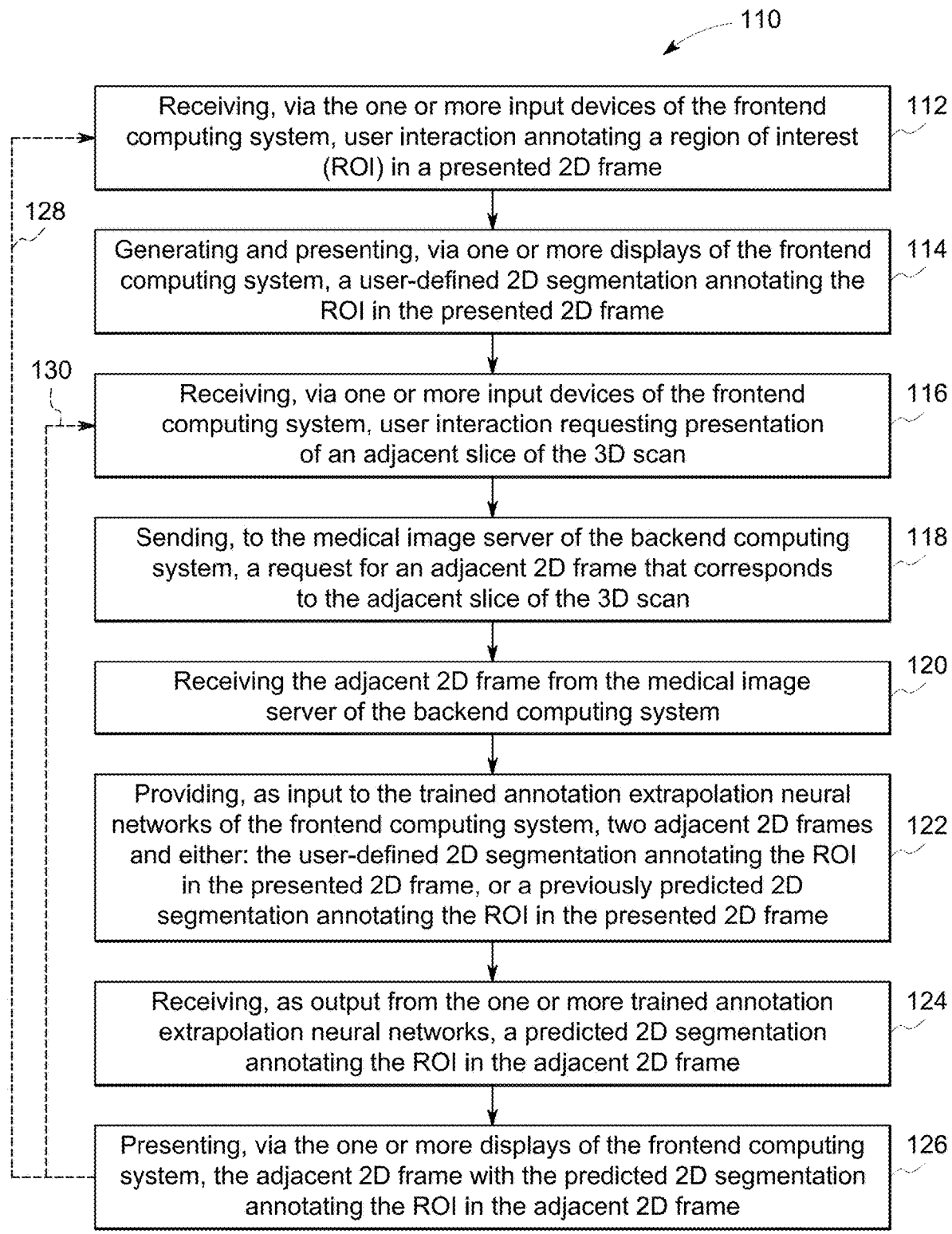
FIG. 4 is a flow diagram of a process whereby the application of the frontend computing system uses trained AENNs of the frontend computing system to perform real-time predictive 2D segmentation of a 2D medical image frame, in accordance with embodiments of the present technique.

FIG. 4 illustrates an embodiment of a process 110 whereby the medical image viewer application 44 of the frontend computing system 16 of the client-server architecture 12 uses the trained AENNs 32 to perform real-time predictive 2D segmentation of a 2D medical image frame using the resources (e.g., the processor 34, the memory 36, the I/O devices 42, the GPU 46) of the frontend computing system 16. For the illustrated embodiment, the process 110 begins with the medical image viewer application 44 receiving (block 112), via at least one of the I/O devices 42 of the frontend computing system 16, user interaction annotating a region of interest (ROI) in a 2D frame being presented on the display of the frontend computing system 16. In response, the medical image viewer application 44 generates and presents (block 114), via a display of the frontend computing system 16, a user-defined 2D segmentation annotating the ROI in the presented 2D frame.

For the illustrated embodiment, the process 110 continues with the medical image viewer application 44 receiving (block 116), via at least one of the I/O devices 42 of the frontend computing system 16, user interaction requesting presentation of an adjacent slice of the 3D scan. In response, the medical image viewer application 44 sends (block 118), to the medical image server 30 of the backend computing system 14, a request for an adjacent 2D frame that corresponds to the adjacent slice of the 3D scan. Subsequently, the medical image viewer application 44 receives (block 120) the adjacent 2D frame from the medical image server 30 of the backend computing system 14.

For the embodiment illustrated in FIG. 4, the process 110 continues with the medical image viewer application 44 providing (block 122), as input to the trained AENNs 32B of the frontend computing system 16, the presented 2D frame, the adjacent 2D frame received in block 120, and the user-defined 2D segmentation generated in block 114. In response to these inputs, the trained AENNs 32B output a predicted 2D segmentation predicting the ROI in the adjacent 2D frame, and the predicted 2D segmentation is received by the medical image viewer application 44 at block 124. Subsequently, the medical image viewer application 44 presents (block 126), via a display of the frontend computing system 16, the adjacent 2D frame with the predicted 2D segmentation indicating the predicted ROI in the adjacent 2D frame.

As indicated by the arrow 128, in certain cases, the medical image viewer application 44 may return to block 112, in response to receiving, via at least one of the I/O devices 42 of the frontend computing system 16, additional user interaction in which the user annotates the ROI in the 2D frame newly presented in block 126. More specifically, the received user input may modify the predicted 2D segmentation previously presented in block 126, for example, to adjust one or more edges of the predicted 2D segmentation to better correspond to the clinician's determination of the actual ROI in the presented frame. In response, the medical image viewer application 44 generates and presents (block 114) via a display of the frontend computing system 16, a second user-defined 2D segmentation annotating the ROI in the presented 2D frame, and then may continue through blocks 116-126, as discussed above.

As indicated by the arrow 130, in certain cases, after presenting the adjacent 2D frame with the predicted 2D segmentation in block 126, the medical image viewer application 44 may return to block 116 in response to receiving, via at least one of the I/O devices 42 of the frontend computing system 16, user interaction requesting presentation of a second adjacent slice of the 3D scan (e.g., a slice that is adjacent to the slice of the frame newly presented in block 126). In this case, the medical image viewer application 44 repeats the actions of blocks 118 and 120 to retrieve the second adjacent 2D frame, based on the user interaction. Then, in a second iteration of block 122, the medical image viewer application 44 provides, as input to the trained AENNs 32B of the frontend computing system 16, the 2D frame newly presented in block 126, the second adjacent 2D frame received in the second iteration of block 120, and the previously predicted 2D segmentation received from the AENNs 32B during the previous iteration of block 124. In response to these inputs, in the second iteration of block 124, the trained AENNs 32 output a second predicted 2D segmentation indicating the predicted ROI in the second adjacent 2D frame, which is received by the medical image viewer application 44. Subsequently, in a second iteration of block 126, the medical image viewer application 44 presents, via a display of the frontend computing system 16, the second adjacent 2D frame with the second predicted 2D segmentation indicating the predicted ROI in the second adjacent 2D frame.

Figure 5A:
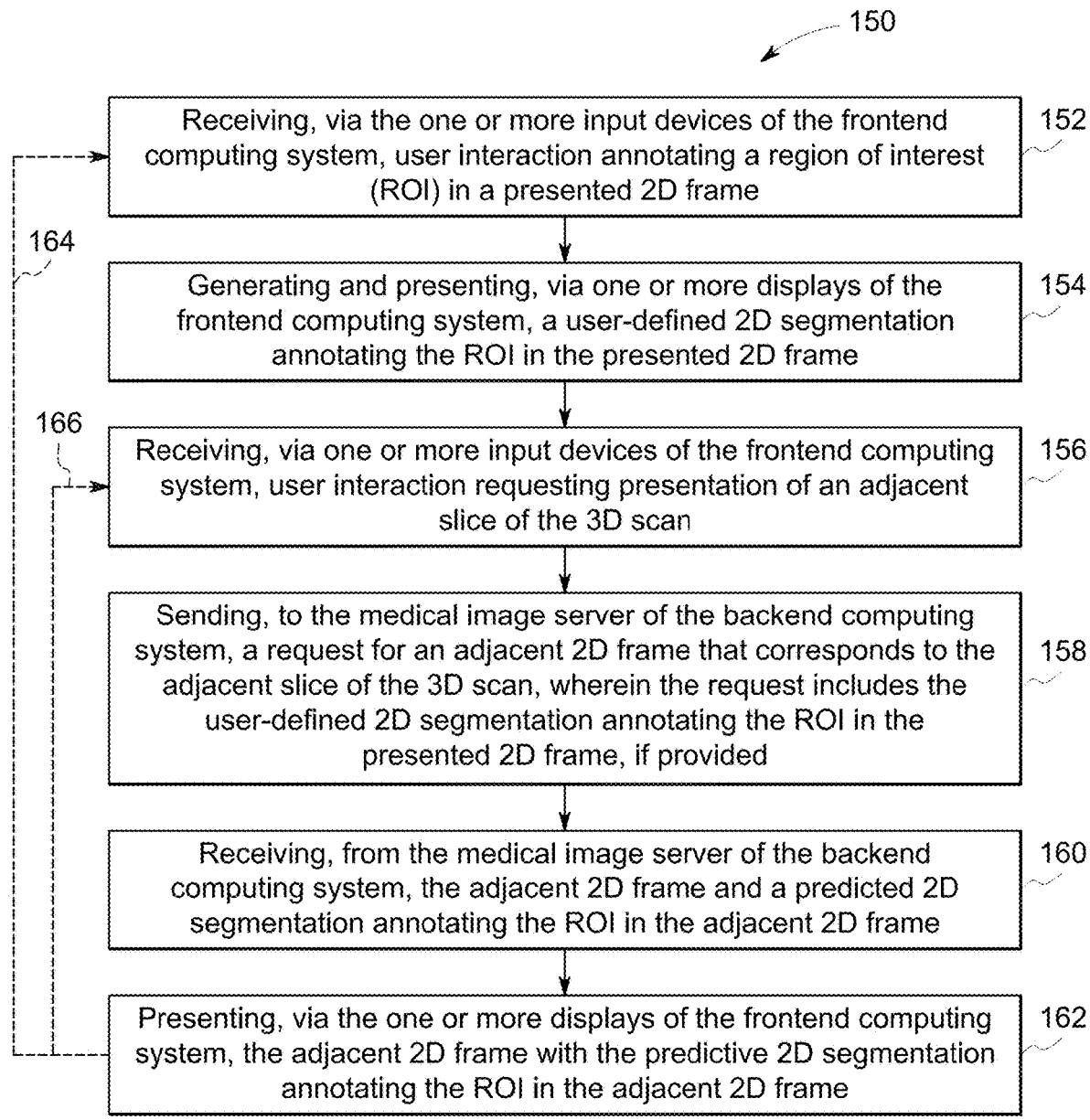
FIG. 5A is a flow diagram of a process whereby the application of the frontend computing system cooperates with the backend computing system to enable the backend computing system to perform backend predictive 2D segmentation, in accordance with embodiments of the present technique.

FIG. 5A illustrates an embodiment of a process 150 whereby the medical image viewer application 44 of the frontend computing system 16 cooperates with the backend computing system 14 to enable the backend computing system 14 to perform backend predictive 2D segmentation. For the illustrated embodiment, the actions of blocks 152, 154, and 156 may proceed as discussed above with respect to FIG. 4. At block 160, the medical image viewer application 44 sends (block 158), to the medical image server 30 of the backend computing system 14, a request for an adjacent 2D frame that corresponds to the adjacent slice of the 3D scan, wherein the request includes the user-defined 2D segmentation generated in block 154. In response, the medical image viewer application 44 receives (block 160), from the medical image server 30, the adjacent 2D frame and a predicted 2D segmentation indicating the predicted ROI in the adjacent 2D frame. Subsequently, the medical image viewer application 44 presents (block 162), via a display of the frontend computing system 16, the adjacent 2D frame with the predicted 2D segmentation indicating the predicted ROI in the adjacent 2D frame.

As indicated by the arrow 164, in certain cases, the medical image viewer application 44 may return to block 152, in response to receiving, via at least one of the I/O devices 42 of the frontend computing system 16, additional user interaction in which the user annotates the ROI in the 2D frame newly presented in block 162. More specifically, the received user input may modify the predicted 2D segmentation received from the medical image server 30 in block 160, for example, to adjust one or more edge of the predicted 2D segmentation to better correspond to the clinician's determination of the actual ROI. In certain embodiments, this user input may be converted into a user-defined 2D segmentation, such as a 2D mask, which may also be compressed in certain cases to limit bandwidth consumption and to reduce latency in communications between the backend computing system 14 and the frontend computing system 16. In response, the medical image viewer application 44 generates and presents (block 154) via a display of the frontend computing system 16, a second user-defined 2D segmentation annotating the ROI in the presented 2D frame, and then continues through blocks 156-162, as discussed above.

As indicated by the arrow 166, in certain cases, after presenting the adjacent 2D frame with the predicted 2D segmentation in block 162, the medical image viewer application 44 may return to block 156 in response to receiving, via at least one of the I/O devices 42 of the frontend computing system 16, user interaction requesting presentation of a second adjacent slice of the 3D scan (e.g., a slice that is adjacent to the slice of the frame newly presented in block 162). In this case, the medical image viewer application 44 sends (block 158), to the medical image server 30, a request for a second adjacent 2D frame that corresponds to the next adjacent slice of the 3D scan, and a user-defined 2D segmentation annotating the ROI in the presented 2D frame is not included, since one was not received from the user for this iteration of the process 150. In response, in a second iteration of block 160, the medical image viewer application 44 receives, from the medical image server 30, the second adjacent 2D frame and a second predicted 2D segmentation indicating the predicted ROI in the second adjacent 2D frame. Subsequently, in a second iteration of block 162, the medical image viewer application 44 presents, via a display of the frontend computing system 16, the second adjacent 2D frame with the second predicted 2D segmentation indicating the predicted ROI in the second adjacent 2D frame.

Figure 5B:
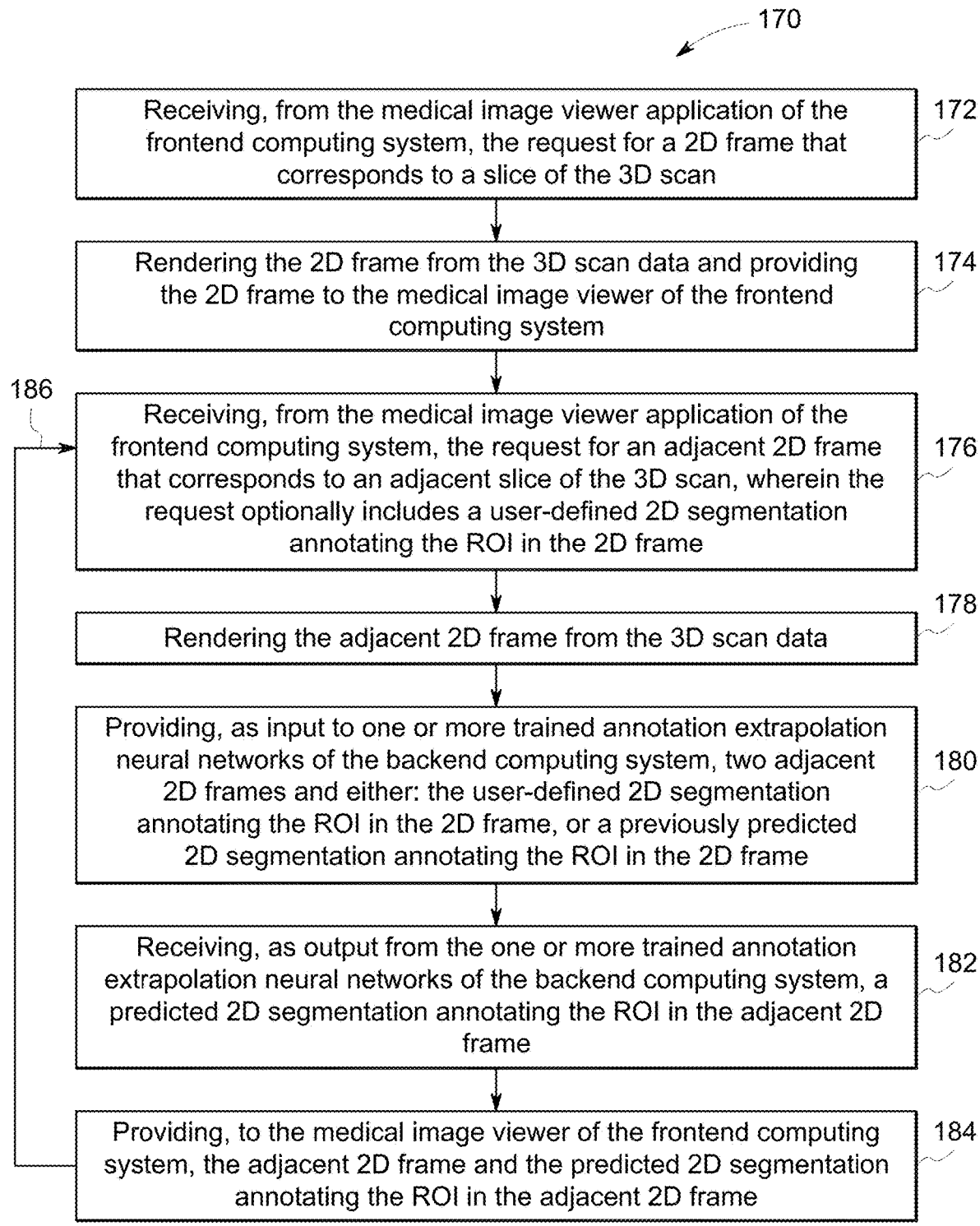
FIG. 5B is a flow diagram of a process whereby the backend computing system uses trained AENNs to perform the backend predictive 2D segmentation, in accordance with embodiments of the present technique.

FIG. 5B illustrates an embodiment of a process 170 whereby medical image server 30 of the backend computing system 14 uses trained AENNs 32A to perform the backend predictive 2D segmentation based on inputs received from the medical image viewer application 44, as discussed with respect to FIG. 5A. As such, the process 170 may be performed using the resources (e.g., the processor 20, the memory 22) of the backend computing system 14. For the embodiment illustrated in FIG. 5B, the process 170 begins with the medical image server 30 receiving (block 172), from the medical image viewer application 44 of the frontend computing system 16, the request for a 2D frame that corresponds to a slice of the 3D scan. In response, the medical image server 30 renders the requested 2D frame from the 3D scan data 28 and provides (block 174) the 2D frame to the medical image viewer application 44 of the frontend computing system 16 for presentation and potential user annotation.

Subsequently, the medical image server 30 receives (block 176) from the medical image viewer application 44, the request for an adjacent 2D frame that corresponds to an adjacent slice of the 3D scan, wherein the request optionally includes a user-defined 2D segmentation annotating the ROI in the 2D frame. In response, the medical image server 30 renders (block 178) the requested adjacent 2D frame from the 3D scan data 28. Additionally, when the request includes the user-defined 2D segmentation, then the medical image server 30 provides (block 180), as input to the trained AENNs 32A of the backend computing system 14, the 2D frame provided in block 174, an adjacent 2D frame rendered in block 178, and the user-defined 2D segmentation received in block 176. In response to these inputs, the trained AENNs 32A output a predicted 2D segmentation indicating the predicted ROI in the adjacent 2D frame, which is received by the medical image server 30 in block 182. Subsequently, the medical image server 30 provides (block 184), to the medical image viewer application 44 of the frontend computing system 16, the adjacent 2D frame and the predicted 2D segmentation indicating the predicted ROI in the adjacent 2D frame to be presented to the clinician for analysis.

As indicated by the arrow 186, in certain cases, the medical image server 30 may return to block 176 in response to receiving, from the medical image viewer application 44, a second request for a second adjacent 2D frame (e.g., a 2D frame adjacent to the adjacent 2D frame rendered in block 178) that corresponds to a second adjacent slice of the 3D scan, wherein the request may or may not include a user-defined 2D segmentation annotating the ROI in the 2D frame. In response, in a second iteration of block 178, the medical image server 30 renders the requested second adjacent 2D frame from the 3D scan data 28. When the request includes the user-defined 2D segmentation, then, in a second iteration of block 180, the medical image server 30 provides, as input to the trained AENNs 32A of the backend computing system 14, the adjacent 2D frame provided in block 184, a second adjacent 2D frame rendered in the second iteration of block 178, and the user-defined 2D segmentation received in the second iteration of block 176. When the request lacks the user-defined segmentation, then, in the second iteration of block 180, the medical image server 30 provides, as input to the trained AENNs 32A of the backend computing system 14, the 2D adjacent frame provided in block 184, the second adjacent 2D frame rendered in the second iteration of block 178, and the previous 2D segmentation received from the AENNs 32A during the previous iteration of block 182. In either case, in response to these inputs, the trained AENNs 32A output a second predicted 2D segmentation indicating the predicted ROI in the second adjacent 2D frame, which is received by the medical image server 30 in a second iteration of block 182. Subsequently, in a second iteration of block 184, the medical image server 30 provides, to the medical image viewer application 44 of the frontend computing system 16, the second adjacent 2D frame and the second predicted 2D segmentation indicating the predicted ROI in the adjacent 2D frame to be presented to the clinician for analysis.

Figure 6:
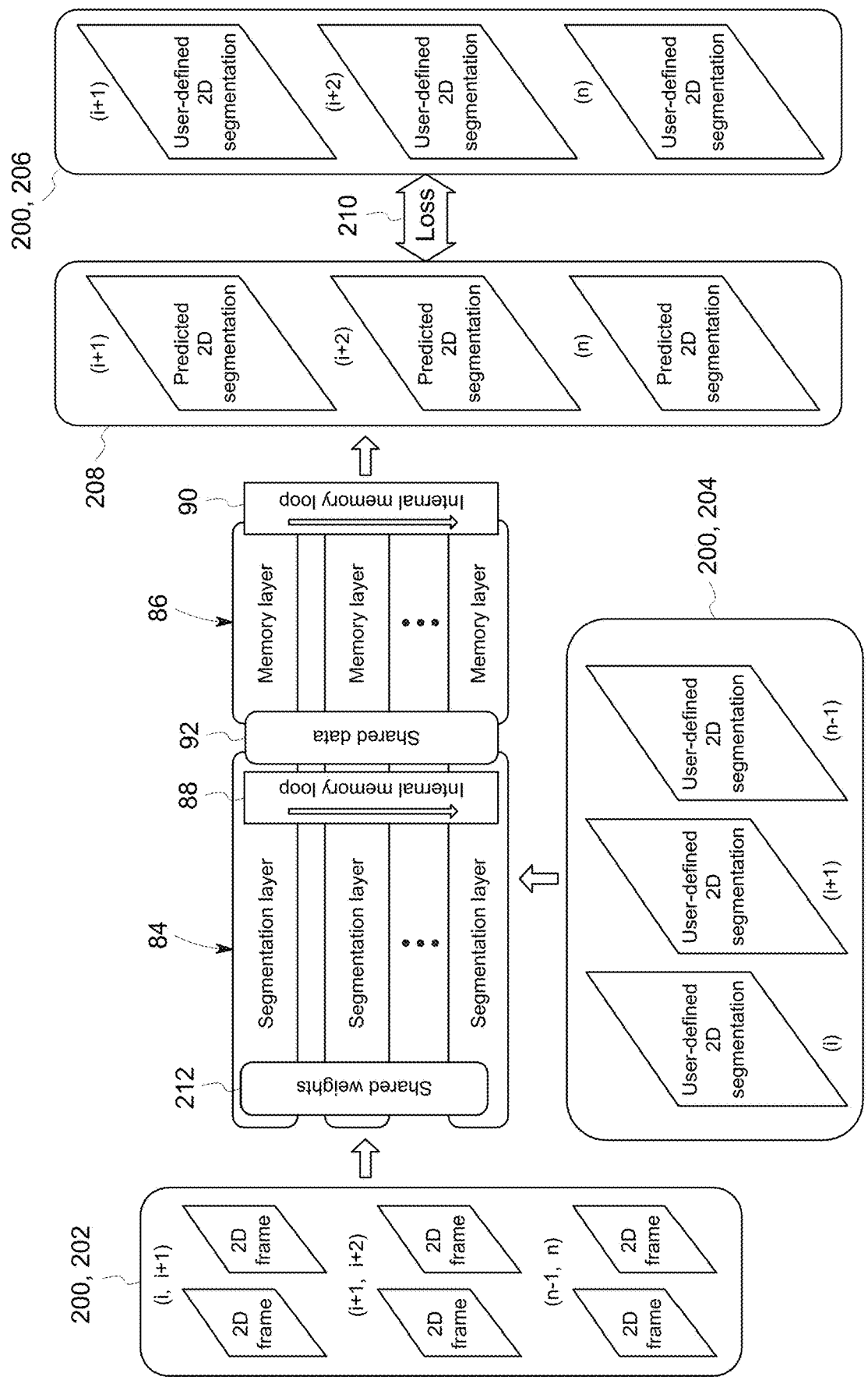
FIG. 6 is a diagram illustrating the training of the AENNs, in accordance with embodiments of the present technique.

FIG. 6 is a diagram illustrating the training of the AENNs 32 (e.g., the backend AENNs 32A or the frontend AENNs 32B). During training, each portion (e.g., each block, each layer) of the set of segmentation neural networks 84 and each portion (e.g., each block, each layer) of the set of memory neural networks 86 are trained using training data 200, which includes a collection of adjacent, clinician-annotated 2D frames rendered from 3D scan data. More specifically, the training data 200 includes pairs of adjacent 2D frames 202, as well as respective clinician-defined 2D segmentations 204 and 206 indicating the ROI within the first and second adjacent frames, respectively. Each of the pairs of adjacent 2D frames 202 are provided as input to the AENNs 32, along with the corresponding user-defined 2D segmentation 204 indicating the ROI in a first frame of the pair, and in response, the AENNs 32 output a respective predictive 2D segmentation 208 that predicts the ROI in the adjacent frame of the pair. A loss function 210 (e.g., dice loss) is computed based on a comparison of the respective predictive 2D segmentation 208 predicting the ROI in the adjacent frame of each pair to the corresponding user-defined 2D segmentation 206 indicating the ROI in the adjacent frame of the pair, which serves as the ground truth. For the illustrated embodiment, the internal output of each layer is also reinjected, generating internal memory loops 88 and 90, such as in a long short-term memory (LSTM) or a convolutional LSTM (e.g., ConvLSTM) neural network architecture. Based on the loss function, gradients may be generated and backpropagated into the AENNs 32 to update one or more shared weights 212 to configure the AENNs 32 for operation. As may be appreciated, this process may proceed through multiple iterations using a large amount of training data 200 until convergence is reached. In certain embodiments, the GPU 46 of the frontend computing system 16, or one or more GPUs of the backend computing system 14, may be used to improve efficiency and/or reduce the run-time of training.

FIGS. 7A-7D are simulated screenshots of an example embodiment of a user interface 220 of the medical image viewer application 44 of the frontend computing system 16 being used to enable predictive 2D segmentation of 2D medical image frames. It may be appreciated that, as discussed above, in certain embodiments, the medical image viewer application 44 may utilize the AENNs 32B of the frontend computing system 16 to perform real-time predictive 2D segmentation of 2D medical image frames, while in other embodiments, the medical image viewer application 44 may cooperate with the backend computing system 14 to enable backend predictive 2D segmentation of 2D medical image frames using the AENNs 32A of the backend computing system 14. Accordingly, these figures are discussed with reference to element illustrated in FIG. 1.

Figure 7A:
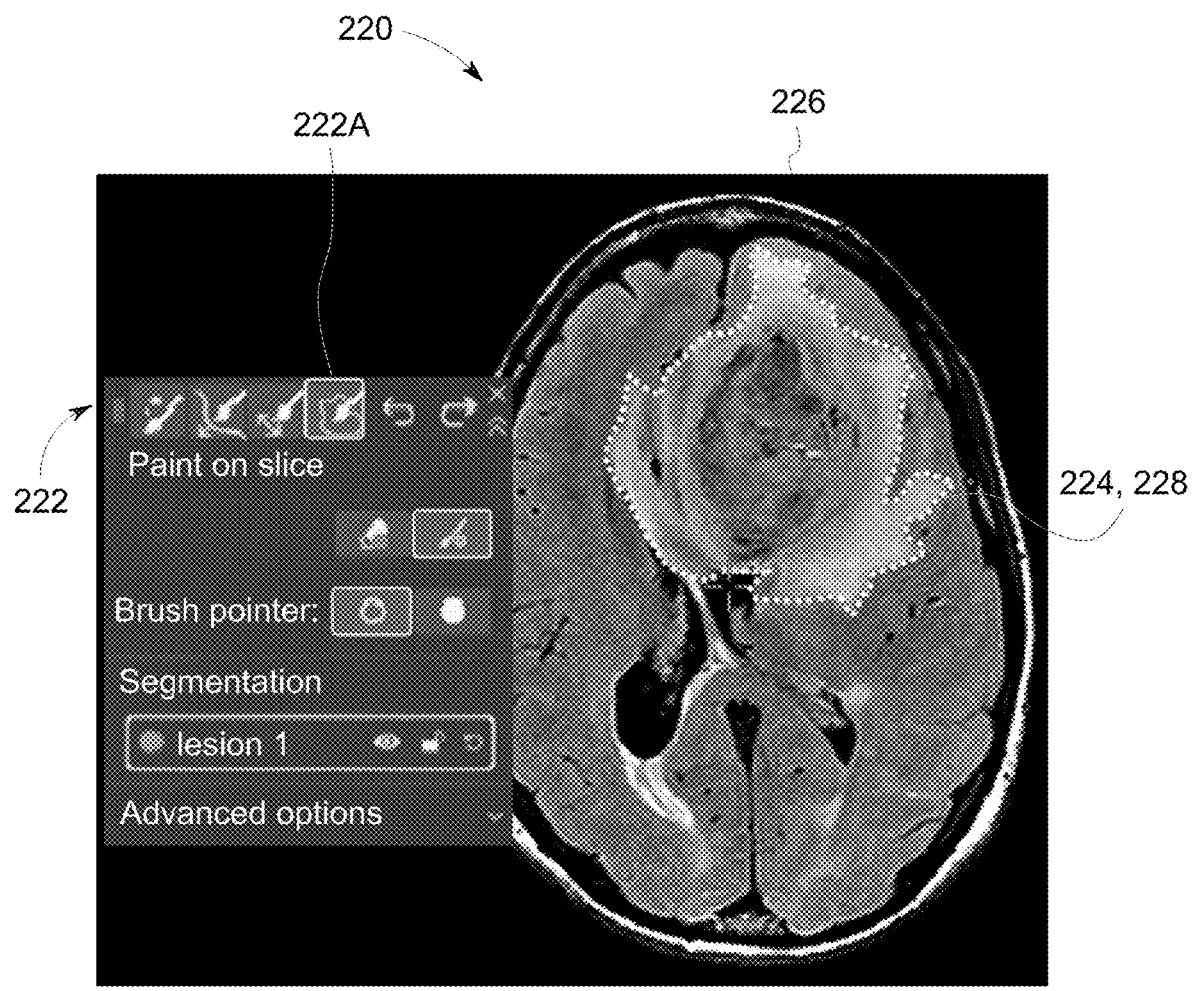
FIGS. 7A, 7B, 7C, and 7D are simulated screenshots of a user interface of the application of the frontend computing system being used to enable predictive 2D segmentation of 2D medical image frames, in accordance with embodiments of the present technique.

In FIG. 7A, the clinician uses one or more tools 222 of the user interface 220 of the medical image viewer application 44 hosted by the frontend computing system 16 in order to annotate a ROI 224 in a presented 2D frame 226, which was rendered by the backend computing system 14 from 3D scan data 28, as discussed above. More specifically, for the illustrated example, the clinician uses one or more suitable I/O devices 42, such as a mouse or touchscreen, to select a particular tool, such as the "paint on slice" tool 222A that is selected in the illustration. Once a suitable tool has been selected, the clinician uses at least one of the I/O devices 42 to define the ROI 224 (e.g., by tracing along the edges of the ROI 224 using the I/O devices 42), and the user interface 220 responds by presenting a user-defined 2D segmentation 228 (e.g., a 2D mask overlaid on the presented frame 226) that indicates the ROI 224 in the presented frame 226 based on the clinician's interactions with the user interface 220.

After annotating the presented frame 226 and presenting the user-defined 2D segmentation 228 indicating the ROI 224, the clinician uses at least one of the I/O devices 42 to provide an input that indicates that the clinician desires to view another frame that is adjacent to the presented frame 226. For example, in certain embodiments, the user interface 220 may be designed to receive inputs from a scroll wheel of a mouse, wherein scrolling in one direction results in the retrieval and presentation of adjacent frames in a first direction, while scrolling the opposite direction results in the retrieval and presentation of adjacent frames in the opposite direction within the 3D scan data. For the illustrated example, the user interface 220 receives input from at least one of the I/O devices 42 requesting the presentation of a first adjacent frame 230, and in response, the first adjacent frame 230 is retrieved from the backend computing system 14 and presented to the clinician with an automatically generated first predicted 2D segmentation 232 that predicts the ROI 234 within the first adjacent frame 230, as illustrated in FIG. 7B.

More specifically, for embodiments directed to real-time predictive 2D segmentation at the frontend computing system 16, after receiving the adjacent image frame 230 from the backend computing system 14, the medical image viewer application 44 provides, as inputs to the AENNs 32B of the frontend computing system 16, the frame 226 presented in FIG. 7A, the first adjacent frame 230 that will be presented in 7B, and the user-defined 2D segmentation 228 presented in FIG. 7A. In response, the medical image viewer application 44 receives, as the output of the AENNs 32B of the frontend computing system 16, the first predicted 2D segmentation 232 that predicts the ROI 234 within the first adjacent frame 230. Additionally, as illustrated in FIG. 7B, the user interface 220 of the medical image viewer application 44 overlays the first predicted 2D segmentation 232 over the first adjacent frame 230 (e.g., as a 2D mask) to illustrate the predicted ROI 234 in the first adjacent frame 230.

For embodiments directed to backend predictive 2D segmentation at the backend computing system 14, upon requesting the first adjacent image frame 230 from the medical image server 30 of the backend computing system 14, the medical image viewer application 44 provides the user-defined 2D segmentation 228 presented in FIG. 7A. The medical image server 30 then, provides, as inputs to the AENNs 32A of the backend computing system 14, the frame 226 presented in FIG. 7A, the first adjacent frame 230 to be presented in FIG. 7B, and the user-defined 2D segmentation 228 presented in FIG. 7A. In response, the medical image server 30 receives, as the output of the AENNs 32A of the backend computing system 14, the first predicted 2D segmentation 232 that predicts the ROI 234 in the first adjacent frame 230. The first adjacent frame 230 and the first predicted 2D segmentation 232 are provided by the backend computing system 14 to the medical image viewer application 44 of the frontend computing system 16. As illustrated in FIG. 7B, the user interface 220 of the medical image viewer application 44 overlays the received first predicted 2D segmentation 232 over the first adjacent frame 230, predicting the ROI 234 in the first adjacent frame 230.

Figure 7B:
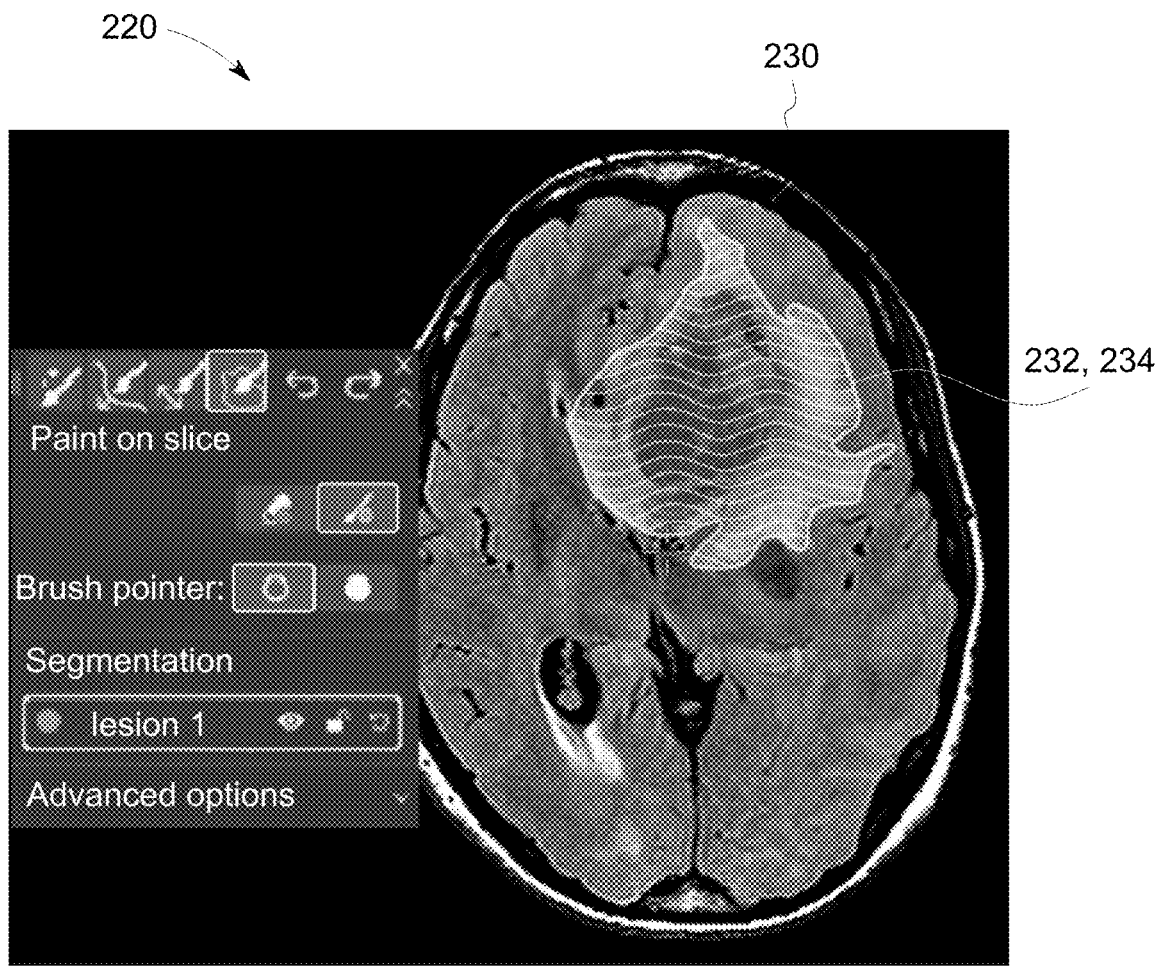

After presenting the first adjacent frame 230 and the first predicted 2D segmentation 232 in FIG. 7B, the clinician uses at least one of the I/O devices 42 to provide an input that indicates that the clinician desires to view another frame that is adjacent to the frame presented in FIG. 7B (e.g., a second adjacent frame). For the illustrated example, the user interface 220 receives input from at least one of the I/O devices 42 requesting the presentation of the second adjacent frame, and in response, the second adjacent frame 236 is retrieved from the backend computing system 14 and presented to the clinician, as illustrated in FIG. 7C.

Figure 7C:
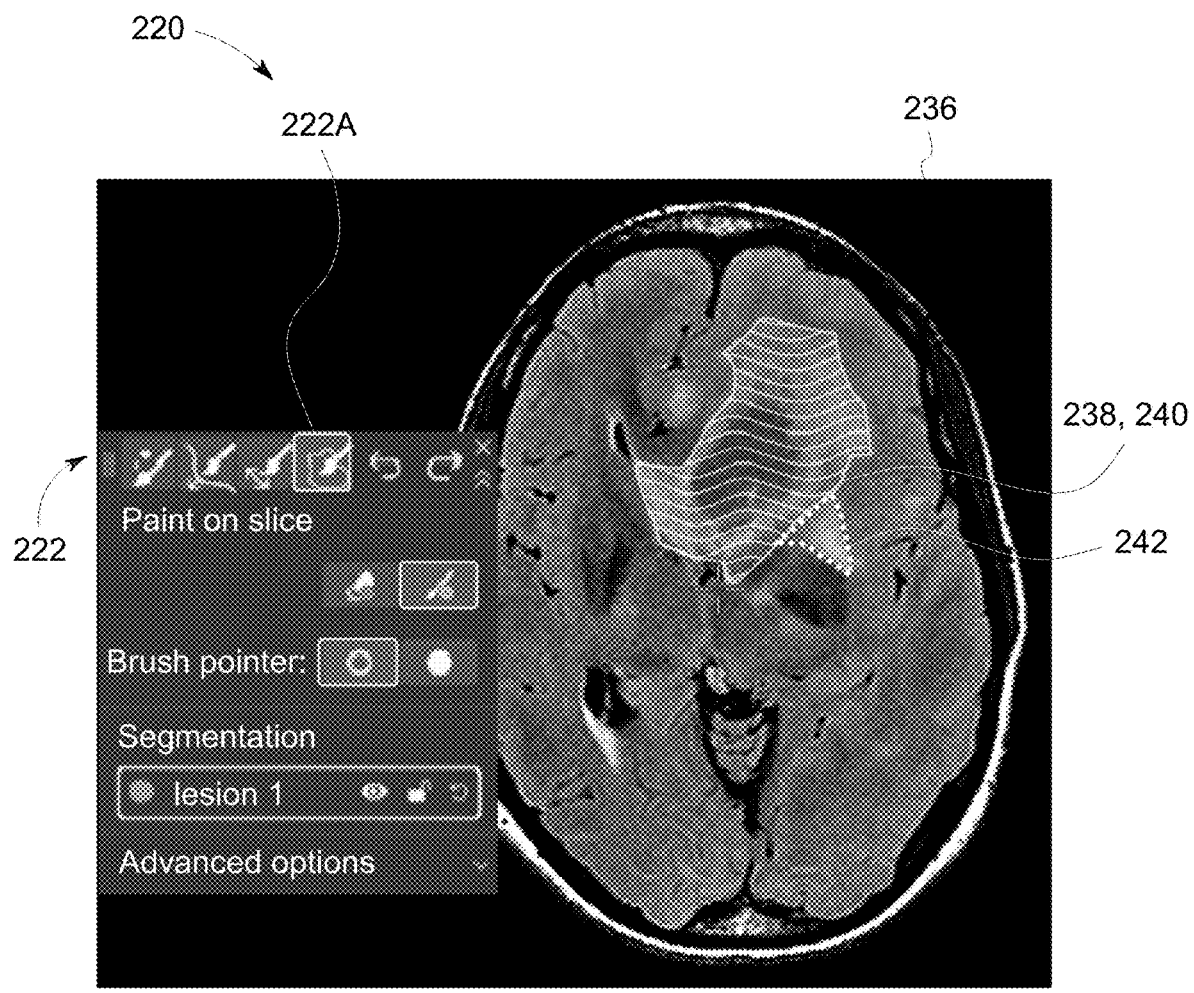

For embodiments directed to real-time predictive 2D segmentation at the frontend computing system 16, after receiving the second adjacent image frame 236 from the backend computing system 14, the medical image viewer application 44 provides, as inputs to the trained AENNs 32B of the frontend computing system 16, the first adjacent frame 230 presented in FIG. 7B, the second adjacent frame 236 to be presented in FIG. 7C, and the predicted 2D segmentation 232 presented in FIG. 7B. In response, the application 44 receives, as the output from the AENNs 32B of the frontend computing system 16, a second predicted 2D segmentation 238 for the second adjacent frame 236. Additionally, as illustrated in FIG. 7C, the user interface 220 of the application 44 overlays the second predicted 2D segmentation 238 over the second adjacent frame 236, predicting the ROI 240 in the second adjacent frame 236.

For embodiments directed to backend predictive 2D segmentation at the backend computing system 14, when requesting the second adjacent image frame 236 from the medical image server 30 of the backend computing system 14, the medical image viewer application 44 does not provide a user-defined 2D segmentation. Instead, the medical image server 30, provides, as inputs to the AENNs 32A of the backend computing system 14, the first adjacent frame 230 presented in FIG. 7B, the second adjacent frame 236 to be presented in FIG. 7C, and the predicted 2D segmentation 232 presented in FIG. 7B. In response, the medical image server 30 receives, as the output of the AENNs 32A of the backend computing system 14, the second predicted 2D segmentation 238 for the second adjacent frame 236. The second adjacent frame 236 and the second predicted 2D segmentation 238 are provided by the backend computing system 14 to the medical image viewer application 44 of the frontend computing system 16. As illustrated in FIG. 7C, the user interface 220 of the application 44 overlays the received second predicted 2D segmentation 238 over the second adjacent frame 236, predicting the ROI 240 in the second adjacent frame 236.

After the user interface 220 presents the second adjacent frame 236 with the second predicted 2D segmentation 238 overlaid, as illustrated in FIG. 7C, the clinician again uses one or more tools 222 of the user interface 220 to modify the annotation of the ROI 240 in the second adjacent frame 236. More specifically, for the illustrated example, the clinician again uses the "paint on slice" tool 222A to define or modify the ROI 240 by tracing along one or more edges of the ROI 240 using the I/O devices 42, indicating areas of the ROI that were not indicated within the second predicted 2D segmentation 238, such as the region 242 of the second adjacent frame 236. Although not illustrated in FIG. 7C, the user interface 220 responds by presenting a second user-defined 2D segmentation (e.g., a 2D mask overlaid on the presented frame 236) that indicates the clinician-modified ROI (e.g., including the newly indicated region 242) in the presented frame 236 based on the clinician's interactions with the user interface 220.

After presenting the second adjacent frame 236 and the second user-defined 2D segmentation in FIG. 7C, the clinician uses at least one of the I/O devices 42 to provide an input that indicates that the clinician desires to view another frame that is adjacent to the frame presented in FIG. 7C (e.g., a third adjacent frame). For the illustrated example, the user interface 220 receives input from at least one of the I/O devices 42 requesting the presentation of the third adjacent frame, and in response, the third adjacent frame 244 is retrieved from the backend computing system 14 and presented to the clinician, as illustrated in FIG. 7D.

Figure 7D:
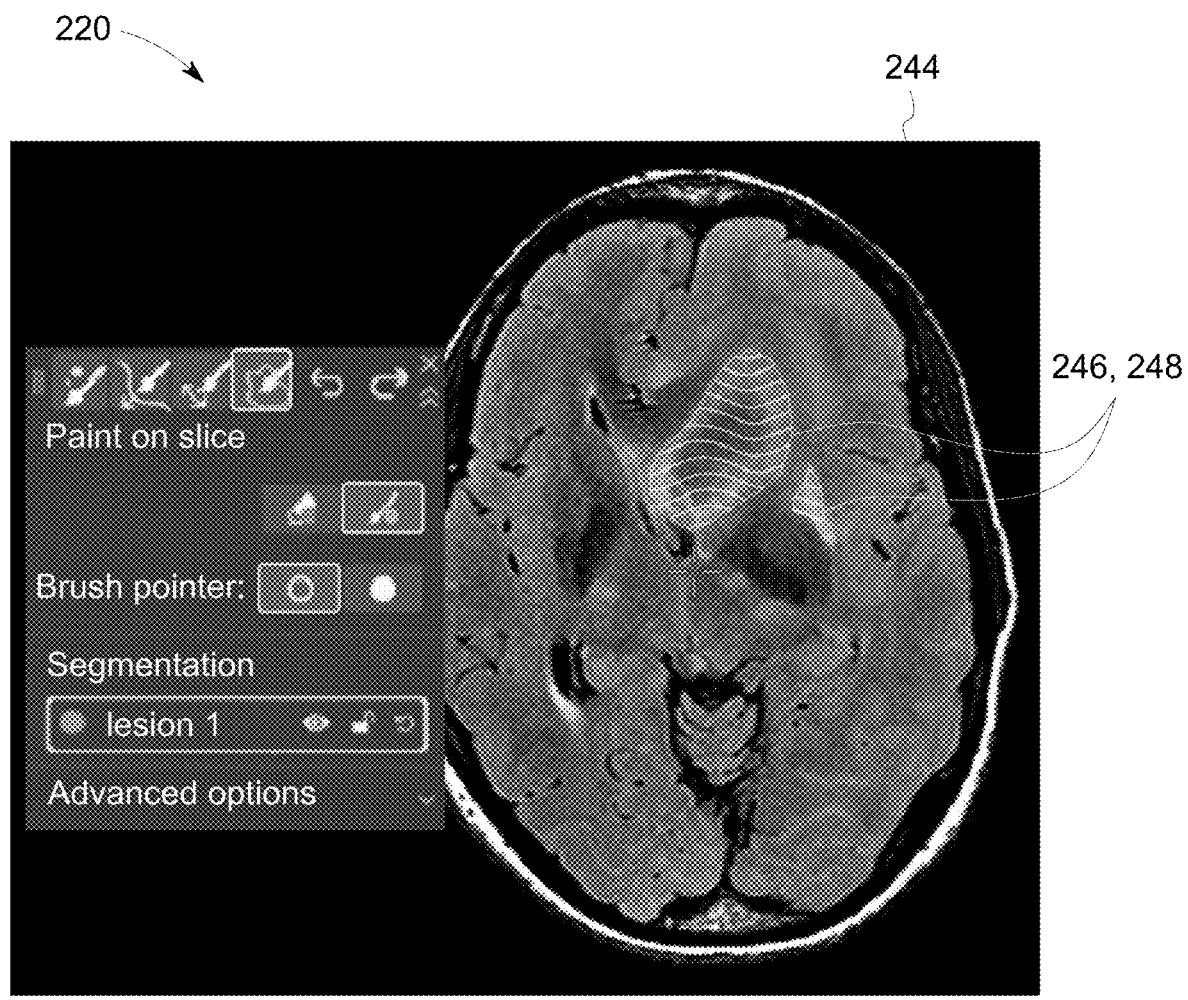

For embodiments directed to real-time predictive 2D segmentation at the frontend computing system 16, after receiving the third adjacent frame 244 from the backend computing system 14, the medical image viewer application 44 provides, as inputs to the AENNs 32B of the frontend computing system 16, the second adjacent frame 236 presented in FIG. 7C, the third adjacent frame 244 to be presented in FIG. 7D, and the second user-defined 2D segmentation discussed with respect to FIG. 7C. In response, the medical image viewer application 44 receives, as the output of the AENNs 32B of the frontend computing system 16, a third predicted 2D segmentation 246 for the third adjacent frame 244. Additionally, as illustrated in FIG. 7D, the user interface 220 of the application 44 overlays the third predicted 2D segmentation 246 over the third adjacent frame 244, predicting the ROI 248 in the third adjacent frame 244.

For embodiments directed to backend predictive 2D segmentation at the backend computing system 14, when requesting the third adjacent image frame 244 from the medical image server 30 of the backend computing system 14, the medical image viewer application 44 provides the second user-defined 2D segmentation discussed with respect to FIG. 7C. The medical image server 30 then, provides, as inputs to the AENNs 32A of the backend computing system 14, the second adjacent frame 236 presented in FIG. 7C, the third adjacent frame 244 to be presented in FIG. 7D, and the second user-defined 2D segmentation determined in FIG. 7C. In response, the medical image server 30 receives, as the output of the AENNs 32A of the backend computing system 14, the third predicted 2D segmentation 246 that predicts the ROI 248 of the third adjacent frame 244. The third adjacent frame 244 and the third predicted 2D segmentation 246 are subsequently provided by the backend computing system 14 to the medical image viewer application 44 of the frontend computing system 16 for presentation to the clinician, as discussed above.

It may be appreciated that, as discussed above, this process can continue to be repeated with respect to all 2D image frames rendered from all slices in the 3D scan data (e.g., a fourth adjacent frame, a fifth adjacent frame, a sixth adjacent frame, and so forth), in accordance with present embodiments. For example, the process may continue with providing, as input to the set of trained AENNs, the third adjacent frame 244 presented in FIG. 7D, a fourth 2D medical image frame rendered from a fourth slice adjacent to the third slice in the 3D medical scan data, and either (i) a second user-defined 2D segmentation indicating (e.g., adjusting, modifying) the predicted ROI in the third adjacent frame 244 or (ii) the third predicted 2D segmentation 246 of FIG. 7D, and receive, as output from the set of trained AENNs, a fourth predicted 2D segmentation indicating a predicted ROI in the fourth 2D medical image frame.

FIGS. 8-12 illustrate examples of predictive 2D segmentations generated by the AENNs 32 during real-time predictive 2D segmentation at the frontend computing system 16 or during backend predictive 2D segmentation at the backend computing system 14. Each example includes a respective series 260 of adjacent 2D frames rendered from respective 3D scan data of a particular anatomical region. Each example also includes a corresponding series 262 of user-defined 2D segmentations that indicate a ROI defined by a clinician in each of the adjacent 2D frames. Each example also includes a corresponding series 264 of predicted 2D segmentations generated by the AENNs 32 that predict the ROI in each of the adjacent 2D frames, with the exception of one indicated user-defined 2D segmentation 266 that was provided as part of the initial inputs to the AENNs 32, as discussed above. That is, for these examples, after receiving only the user-defined 2D segmentation 266, the AENNs 32 continue to generate the predicted 2D segmentations of the series 264 that predict the ROI in each of the series 260 of adjacent 2D frames as the clinician traverses the 3D scan data, as discussed above. Therefore, a visual comparison of the series 262 of user-defined 2D segmentations to the series 264 of predicted 2D segmentations provides an indication of the quality of the predicted 2D segmentations generated by the AENNs 32.

Figure 8:
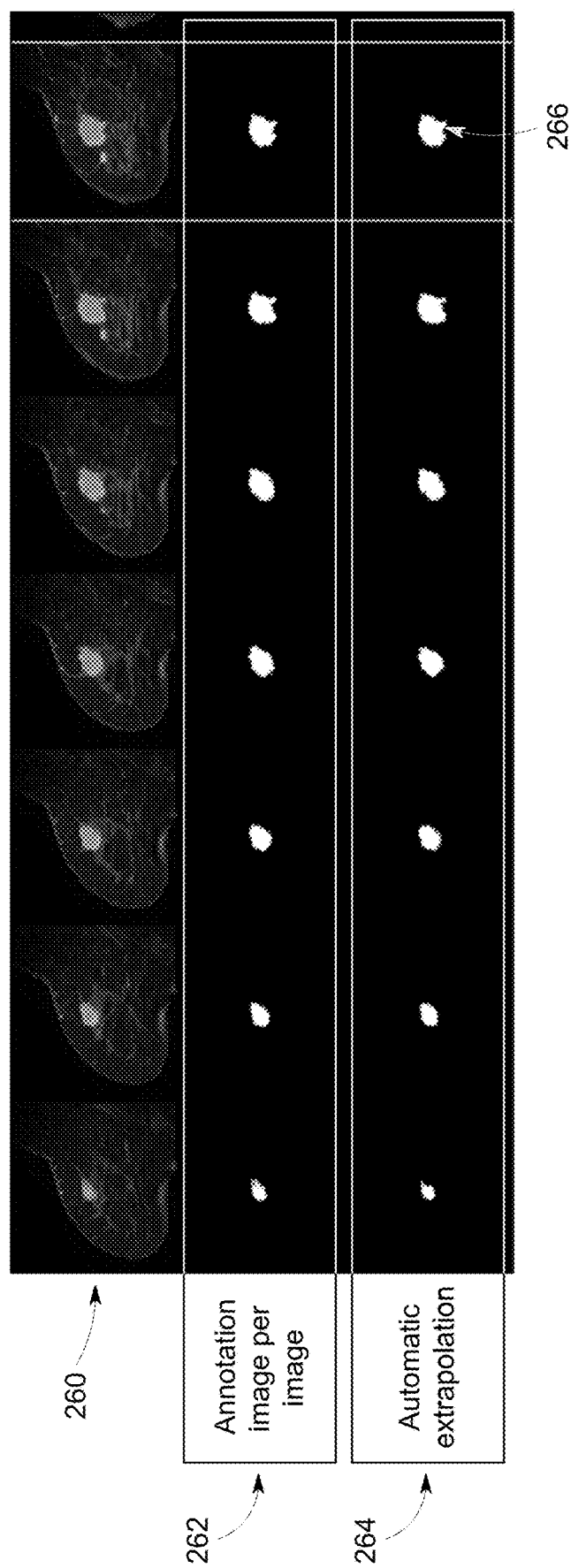
FIGS. 8, 9, 10, 11, and 12 are examples that include a series of adjacent 2D medical image frames, corresponding user-defined 2D segmentations for each of the 2D medical image frames, and corresponding predicted segmentations generated by the AENNs for each of the 2D medical image frames, in accordance with embodiments of the present technique.
Figure 9:
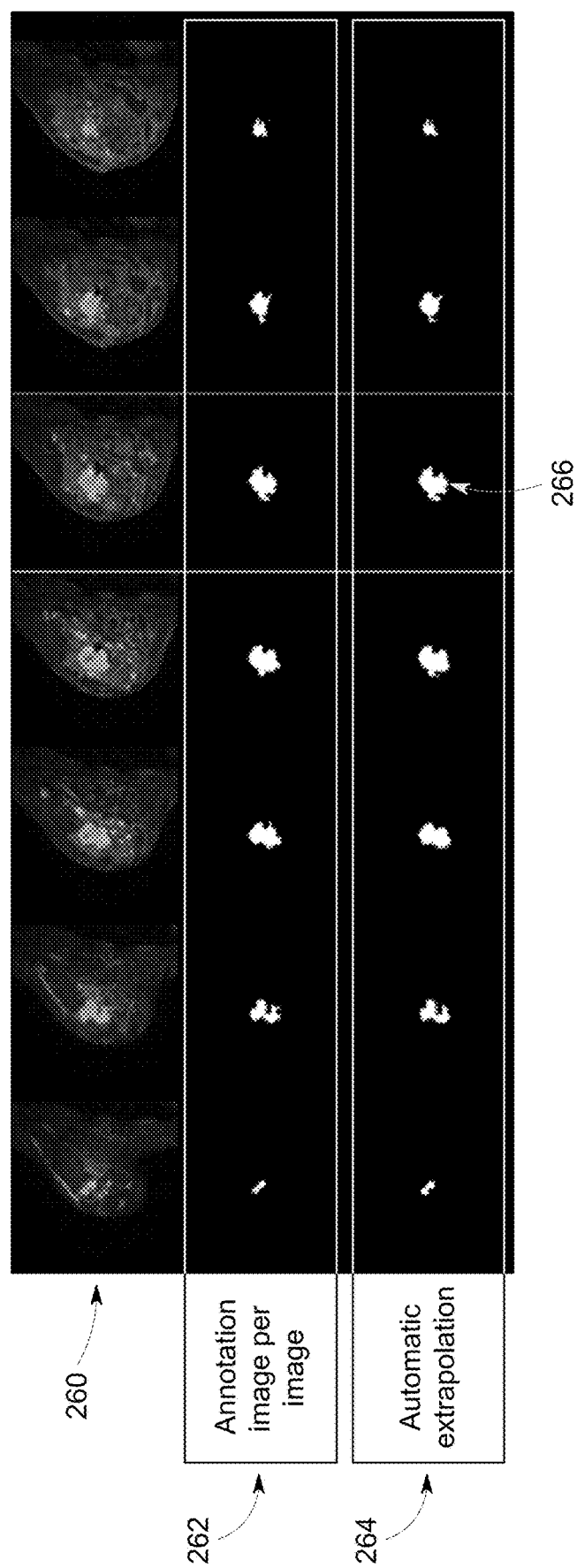
Figure 10:
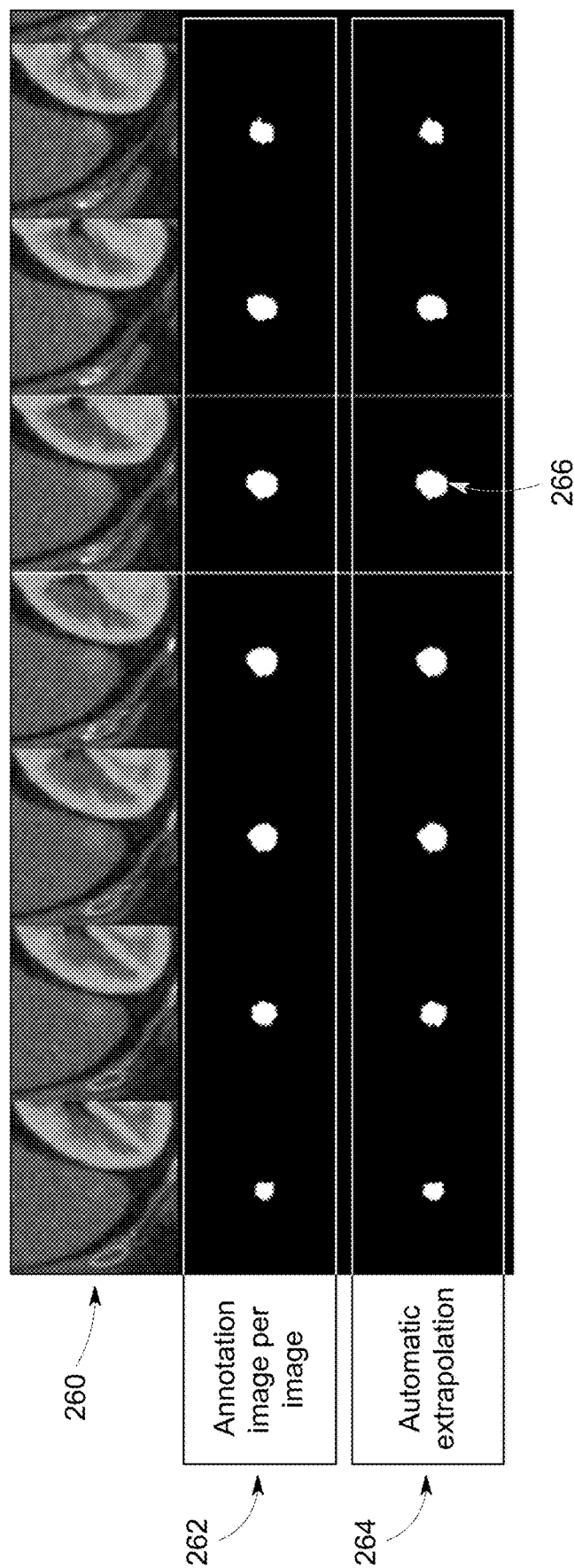
Figure 11:
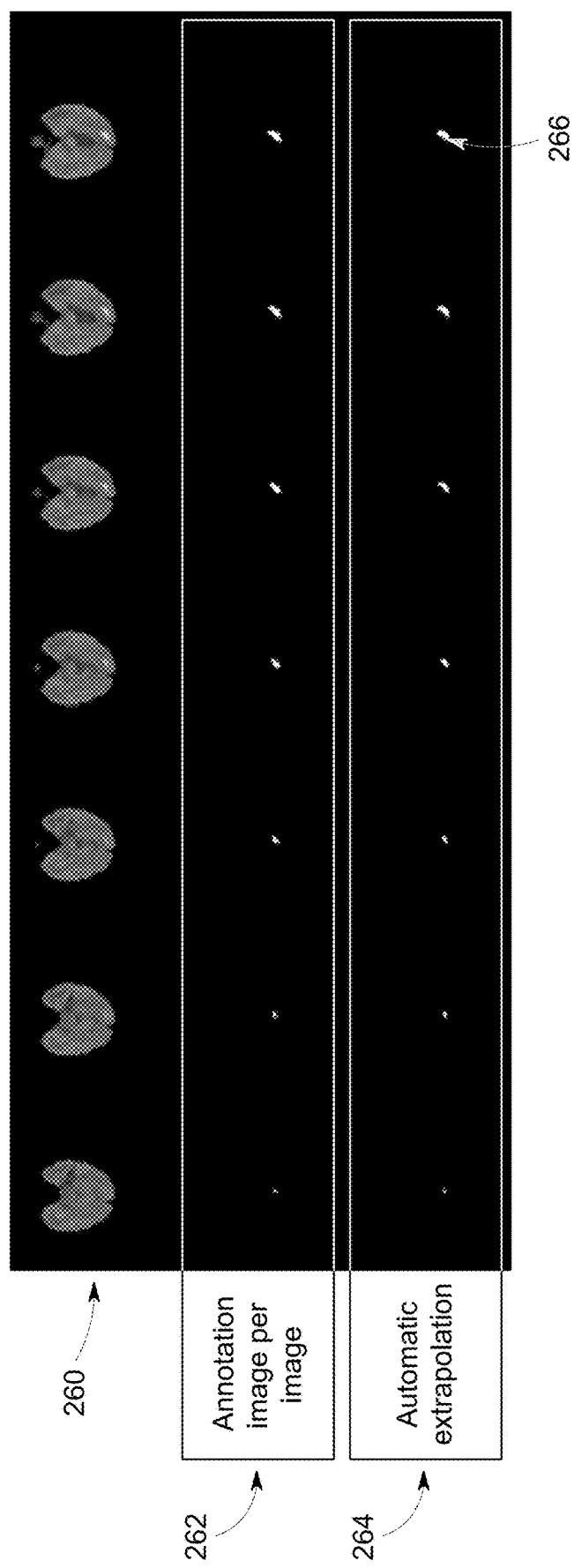
Figure 12:
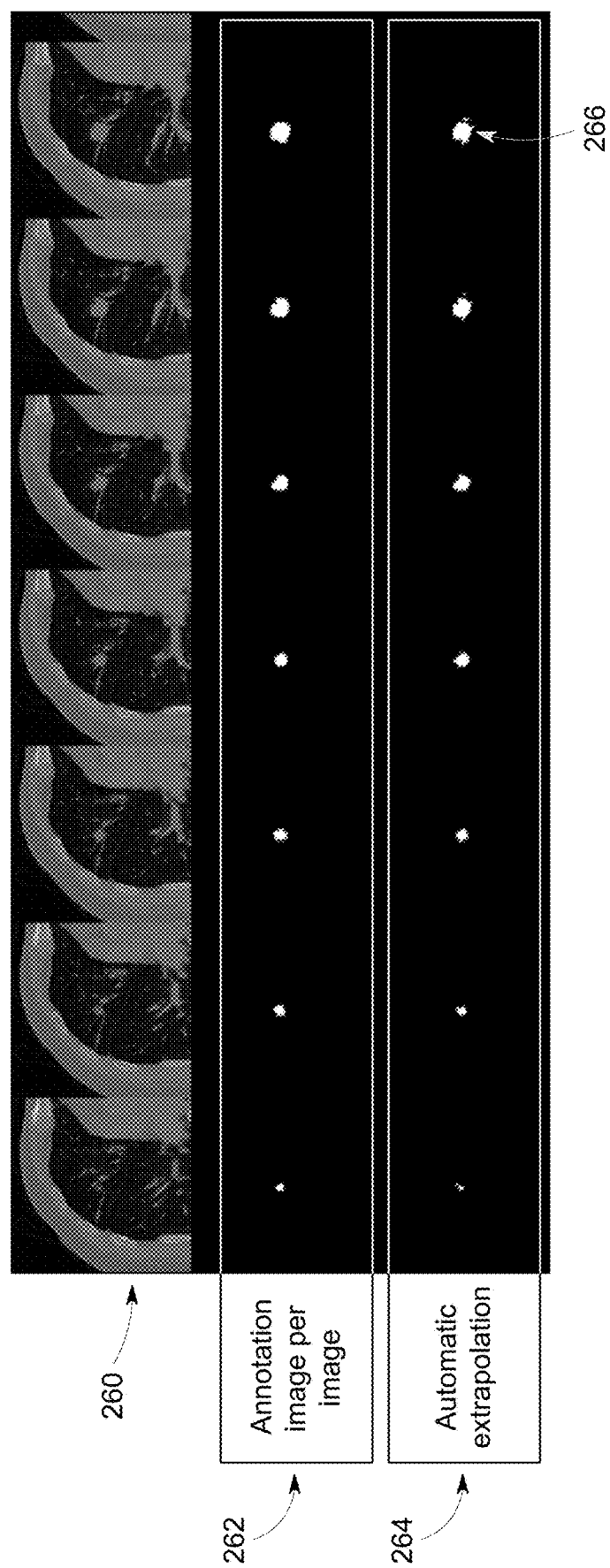

More specifically, the series 260A and 260B of adjacent frames of the examples of FIGS. 8 and 9 are rendered from computed tomography (CT) scans of breast tissue, the series 260 of adjacent frames of the example of FIG. 10 are rendered from CT scans of liver tissue, while the series 260 of adjacent frames of the examples of FIGS. 11 and 12 are rendered from magnetic resonance (MR) scans of brain tissue. As represented within the examples of FIGS. 8-12, the predicted 2D segmentations accurately predict the ROI in each of the series 260 of adjacent frames, regardless of whether the ROI is a lesion, a cyst, a tumor, or other abnormality or anatomical feature, and regardless of the shape or modality of the ROI.

Technical effects of the present disclosure include a client-server architecture and methods for extrapolating a predictive 2D segmentation that indicates a predicted ROI in a 2D medical image frame rendered from 3D medical scan data, wherein the predictive 2D segmentation is generated based on a user-defined 2D segmentation that annotates the ROI in another image frame rendered from the 3D medical scan data. Present embodiments operate via extrapolation, in which a single user-defined 2D segmentation of a medical image frame is extrapolated using deep learning techniques to generate predicted 2D segmentations for all of the other image frames within a set of 3D medical scan data. This enables present embodiments to effectively annotate the ROI in a series of 2D medical image frames with minimal input from a clinician to provide the initial user-defined 2D segmentation, reducing the amount of time the clinician spends analyzing the 3D medical scan data, as well as reducing the number of inputs that the clinician needs to provide to annotate the ROI in the 3D medical scan data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computing system for performing real-time predictive two-dimensional (2D) segmentation of 2D medical image frames, comprising:
   at least one networking device;
   at least one memory configured to store an application that includes a user interface and a set of trained annotation extrapolation neural networks (AENNs); and
   at least one processor configured to execute stored instructions to perform actions comprising:
      receiving, via the at least one networking device, a first two-dimensional (2D) medical image frame, and a second 2D medical image frame adjacent to the first 2D medical image frame within a set of three-dimensional (3D) medical scan data;
      presenting, via the user interface, the first 2D medical image frame;
      receiving, via the user interface, a first user interaction annotating a region of interest (ROI) in the first 2D medical image frame to generate a first user-defined 2D segmentation mask;
      presenting, via the user interface, the first 2D medical image frame with a first user-defined 2D segmentation mask overlaid to annotate the ROI in the first 2D medical image frame based on the first user interaction;
      providing, as input to the set of trained AENNs, the first 2D medical image frame, the second 2D medical image frame, and the first user-defined 2D segmentation mask;
      receiving, as output from the set of trained AENNs, a first predicted 2D segmentation indicating a predicted ROI in the second 2D medical image frame, wherein the set of trained AENNS is configured to predict, via extrapolation, the first predicted 2D segmentation and any other predicted 2D segmentations of 2D medical images frames from within the set of 3D medical scan data based solely on the first user-defined 2D segmentation mask or a previously predicted 2D segmentation extrapolated from the first-user defined 2D segmentation; and
      presenting, via the user interface, the second 2D medical image frame with the first predicted 2D segmentation overlaid to indicate the predicted ROI in the second 2D medical image frame.

2. The computing system of claim 1, wherein the at least one networking device is configured to communicatively couple the computing system to a medical imaging server, and wherein the first 2D medical image frame and the second 2D medical image frame are received, via the at least one networking device, from the communicatively coupled medical imaging server.

3. The computing system of claim 2, wherein before receiving the second 2D medical image frame, the at least one processor is configured to execute the stored instructions to perform actions comprising:
receiving, via the user interface, a second user interaction requesting presentation of the second 2D medical image frame, and in response, requesting and receiving, from the medical imaging server, the second 2D image frame.

4. The computing system of claim 1, wherein the at least one processor is configured to execute the stored instructions to perform actions comprising:
receiving, via the at least one networking device, a third 2D medical image frame adjacent to the second 2D medical image frame within the set of 3D medical scan data;
providing, as input to the set of trained AENNs, the second 2D medical image frame, the third 2D medical image frame, and the first predicted 2D segmentation;
receiving, as output from the set of trained AENNs, a second predicted 2D segmentation indicating a predicted ROI in the third 2D medical image frame; and
presenting, via the user interface, the third 2D medical image frame with the second predicted 2D segmentation overlaid to indicate the predicted ROI in the third 2D medical image frame.

5. The computing system of claim 1, wherein the at least one processor is configured to execute the stored instructions to perform actions comprising:
receiving, via the user interface, a second user interaction annotating the ROI in the second 2D medical image frame; and
presenting, via the user interface, the second 2D medical image frame with a second user-defined 2D segmentation mask overlaid to annotate the ROI in the second 2D medical image frame based on the second user interaction.

6. The computing system of claim 5, wherein the at least one processor is configured to execute the stored instructions to perform actions comprising:
receiving, via the at least one networking device, a third 2D medical image frame adjacent to the second 2D medical image frame within the set of 3D medical scan data;
providing, as input to the set of trained AENNs, the second 2D medical image frame, the third 2D medical image frame, and the second user-defined 2D segmentation mask;
receiving, as output from the set of trained AENNs, a second predicted 2D segmentation indicating a predicted ROI in the third 2D medical image frame; and
presenting, via the user interface, the third 2D medical image frame with the second predicted 2D segmentation overlaid to indicate the predicted ROI in the third 2D medical image frame.

7. The computing system of claim 1, wherein the at least one processor comprises one or more processors of a graphics processing unit (GPU).

8. A method for predictive two-dimensional (2D) segmentation of medical image frames, comprising:
determining a first two-dimensional (2D) medical image frame from a set of three-dimensional (3D) medical scan data;
determining a first user-defined 2D segmentation mask that annotates a region of interest (ROI) in the first 2D medical image frame based on a first user interaction;
determining a second 2D medical image frame adjacent to the first 2D medical image frame in the set of 3D medical scan data;
providing, as input to a set of trained annotation extrapolation neural networks (AENNs), the first 2D medical image frame, the second 2D medical image frame, and the first user-defined 2D segmentation mask; and
receiving, as output from the trained AENNs, a first predicted 2D segmentation indicating a predicted ROI in the second 2D medical image frame, wherein the set of trained AENNS is configured to predict, via extrapolation, the first predicted 2D segmentation and any other predicted 2D segmentations of 2D medical images frames from within the set of 3D medical scan data based solely on the first user-defined 2D segmentation mask or a previously predicted 2D segmentation extrapolated from the first-user defined 2D segmentation.

9. The method of claim 8, comprising:
determining a third 2D medical image frame adjacent to the second 2D medical image frame in the set of 3D medical scan data;
providing, as input to the set of trained AENNs, the second 2D medical image frame, the third 2D medical image frame, and the first predicted 2D segmentation; and
receiving, as output from the trained AENNs, a second predicted 2D segmentation indicating a predicted ROI in the third 2D medical image frame.

10. The method of claim 8, comprising:
determining a third 2D medical image frame adjacent to the second 2D medical image frame in the set of 3D medical scan data;
determining a second user-defined 2D segmentation mask that annotates a ROI in the second 2D medical image frame based on a second user interaction;
providing, as input to the set of trained AENNs, the second 2D medical image frame, the third 2D medical image frame, and the second user-defined mask 2D segmentation; and
receiving, as output from the trained AENNs, a second predicted 2D segmentation indicating a predicted ROI in the third 2D medical image frame.

11. The method of claim 8, wherein determining the first 2D image frame and determining the second 2D image frame comprises receiving the first 2D image frame and the second 2D image frame from a communicatively coupled backend computing device that stores the set of 3D medical scan data and that renders the first 2D image frame and the second 2D image frame from the set of 3D medical scan data, and
wherein determining the first user-defined 2D segmentation mask comprises receiving, via a user interface, the first user interaction annotating the ROI in the first 2D medical image frame and generating the first user-defined 2D segmentation mask based on the first user interaction.

12. The method of claim 11, comprising:
presenting, via the user interface, the first 2D medical image frame with the first user-defined 2D segmentation mask overlaid to annotate the ROI in the first 2D medical image frame; and
presenting, via the user interface, the second 2D medical image frame with the first predicted 2D segmentation overlaid to indicate the predicted ROI in the second 2D medical image frame.

13. The method of claim 8, wherein determining the first 2D image frame and determining the second 2D image frame comprises rendering the first 2D image frame and the second 2D image frame from the set of 3D medical scan data, and wherein the determining the first user-defined 2D segmentation mask comprises receiving, from a medical image viewer application, the first user-defined 2D segmentation generated by the medical image viewer application based on the first user interaction.

14. The method of claim 13, comprising:

providing, to the medical image viewer application, the first 2D medical image frame; and providing, to the medical image viewer application, the second 2D medical image frame and the first predicted 2D segmentation.

15. A computing system, comprising:

at least one memory configured to store a set of trained annotation extrapolation neural networks (AENNs); and at least one processor configured to execute stored instructions to perform actions comprising:

providing, as input to the set of trained AENNs, a first two-dimensional (2D) medical image frame rendered from a first slice of three-dimensional (3D) medical scan data, a second 2D medical image frame rendered from a second slice adjacent to the first slice in the 3D medical scan data, and a first user-defined 2D segmentation mask annotating a region of interest (ROI) in the first 2D medical image frame;

receiving, as output from the set of trained AENNs, a first predicted 2D segmentation indicating a predicted ROI in the second 2D medical image frame, wherein the set of trained AENNS is configured to predict, via extrapolation, the first predicted 2D segmentation and any other predicted 2D segmentations of 2D medical images frames from within the set of 3D medical scan data based solely on the first user-defined 2D segmentation mask or a previously predicted 2D segmentation extrapolated from the first-user defined 2D segmentation;

providing, as input to the set of trained AENNs, the second 2D medical image frame, a third 2D medical image frame rendered from a third slice adjacent to the second slice in the 3D medical scan data, and the first predicted 2D segmentation; and receiving, as output from the set of trained AENNs, a second predicted 2D segmentation indicating a predicted ROI in the third 2D medical image frame.

16. The computing system of claim 15, wherein the set of trained AENNs comprises a set of segmentation neural networks and a set of memory neural networks that share data with one another and include respective internal memory loops.

17. The computing system of claim 15, wherein the set of trained AENNs comprises a long short-term memory (LSTM) neural network.

18. The computing system of claim 15, wherein, before providing the first and second medical image frames and the first user-defined 2D segmentation mask as input to the set of trained AENNs, the at least one processor is configured to execute the stored instructions to perform actions comprising:

training a set of AENNs based on a set of training data to generate the trained AENNs, wherein the set of training data comprises pairs of adjacent 2D medical images and corresponding user-defined 2D segmentations annotating a respective ROI in each of the adjacent pairs of 2D medical images.

19. The computing system of claim 15, wherein the at least one processor is configured to execute the stored instructions to perform actions comprising:

providing, as input to the set of trained AENNs, the third 2D medical image frame, a fourth 2D medical image frame rendered from a fourth slice adjacent to the third slice in the 3D medical scan data, and either (i) a second user-defined 2D segmentation mask indicating the predicted ROI in the third 2D medical image frame or (ii) the second predicted 2D segmentation; and receiving, as output from the set of trained AENNs, a third predicted 2D segmentation indicating a predicted ROI in the fourth 2D medical image frame.

* * * * *